US010179834B2

(12) United States Patent
Blencowe et al.

(10) Patent No.: US 10,179,834 B2
(45) Date of Patent: Jan. 15, 2019

(54) BIODEGRADABLE NETWORK POLYMERS FOR REGENERATIVE MEDICINE AND TISSUE ENGINEERING

(71) Applicant: The University of Melbourne, Melbourne, Victoria (AU)

(72) Inventors: Anton Blencowe, Melbourne (AU); Berkay Ozcelik, Melbourne (AU); Greg Guanghua Qiao, Melbourne (AU)

(73) Assignee: The University of Melbourne, Melbourne, Victoria (AU)

( * ) Notice: Subject to any disclaimer, the term of this patent is extended or adjusted under 35 U.S.C. 154(b) by 14 days.

(21) Appl. No.: 14/783,838

(22) PCT Filed: Apr. 10, 2014

(86) PCT No.: PCT/AU2014/000391
§ 371 (c)(1),
(2) Date: Oct. 9, 2015

(87) PCT Pub. No.: WO2014/165917
PCT Pub. Date: Oct. 16, 2014

(65) Prior Publication Data
US 2016/0060392 A1    Mar. 3, 2016

(30) Foreign Application Priority Data
Apr. 10, 2013  (AU) .................................. 2013901223

(51) Int. Cl.
| C08G 63/66 | (2006.01) |
| A61L 27/18 | (2006.01) |
| A61L 27/56 | (2006.01) |
| A61L 27/58 | (2006.01) |
| A61L 31/06 | (2006.01) |
| C08G 65/34 | (2006.01) |
| C08J 9/00 | (2006.01) |
| C08L 71/00 | (2006.01) |
| C12N 5/00 | (2006.01) |
| C08G 65/332 | (2006.01) |

(52) U.S. Cl.
CPC ............. *C08G 63/66* (2013.01); *A61L 27/18* (2013.01); *A61L 27/56* (2013.01); *A61L 27/58* (2013.01); *A61L 31/06* (2013.01); *C08G 65/3322* (2013.01); *C08G 65/3324* (2013.01); *C08G 65/34* (2013.01); *C08J 9/00* (2013.01); *C08L 71/00* (2013.01); *C12N 5/0018* (2013.01); *C08J 2371/08* (2013.01); *C08L 2201/06* (2013.01); *C08L 2203/02* (2013.01); *C08L 2203/16* (2013.01)

(58) Field of Classification Search
CPC .................................................... C08G 63/66
See application file for complete search history.

(56) References Cited

U.S. PATENT DOCUMENTS

| 4,110,276 A | 8/1978 | DesMarais |
| 2004/0230309 A1 | 11/2004 | DiMauro et al. |
| 2005/0250914 A1 | 11/2005 | Stumbe et al. |
| 2009/0028957 A1* | 1/2009 | Daniloff .............. A61L 24/0042 424/501 |
| 2011/0124765 A1* | 5/2011 | Yang ...................... C08G 63/52 522/87 |
| 2012/0178824 A1 | 7/2012 | König et al. |

FOREIGN PATENT DOCUMENTS

| CN | 1446109 A | 10/2003 |
| EP | 0 696 605 A1 | 2/1996 |
| JP | S58-160316 A | 9/1983 |
| JP | 2003274800 A * | 9/2003 |
| JP | 2004-211008 A | 7/2004 |
| JP | 2006-517842 A | 8/2006 |
| JP | 2007-517543 A | 7/2007 |
| JP | 2007-204614 A | 8/2007 |
| JP | H08-059811 A | 3/2008 |
| WO | WO 98/30617 A1 | 7/1998 |
| WO | WO 02/11781 A1 | 2/2002 |
| WO | WO 2004/020503 A1 | 3/2004 |
| WO | WO 2005/051316 A2 | 6/2005 |

OTHER PUBLICATIONS

CAS Registry entry for Registry No. 42503-45-7, which entered STN on Nov. 16, 1984 (Year: 1984).*
CAS Registry entry for Registry No. 50586-59-9, which entered STN on Nov. 16, 1984 (Year: 1984).*
CAS Registry entry for Registry No. 216316-56-2, which entered STN on Dec. 31, 1998 (Year: 1998).*
CAS Registry entry for Registry No. 58991-77-8, which entered STN on Nov. 16, 1984 (Year: 1984).*
Nair et al. Prog. Polym. Sci. 2007, 32, 762-798 (Year: 2007).*
Vert, Biomacromolecules 2005, 6, 538-546 (Year: 2005).*
Office Action in Japanese Patent Application No. 2016-506730, dated Oct. 13, 2017.
Australian Examination Report in related Australian Patent Application No. 2014252769, dated Nov. 18, 2016 (in 3 pages).
Ozcelik, et al. 2013 "Ultrathin chitosan—poly(ethylene glycol) hydrogel films for corneal tissue engineering" *Acta Biomaterialia* 9: 6594-6605.
Supplementary European Search Report in related European Application No. EP 14 78 2252 dated Nov. 15, 2016 (in 11 pages).
Office Action issued in Chinese Application No. 201480032915.9, dated Jan. 17, 2018.

* cited by examiner

*Primary Examiner* — Matthew P Coughlin
(74) *Attorney, Agent, or Firm* — Knobbe, Martens, Olson & Bear, LLP

(57) ABSTRACT

The disclosure relates to biodegradable polyether network polymers crosslinked via ester linkages, to substrates, implants and scaffolds comprising the biodegradable polyether network polymers, to methods for preparing such network polymers, implants and scaffolds, and to methods of using substrates, implants and scaffolds comprising the network polymers, particularly for culturing cells and regenerating tissue.

14 Claims, 18 Drawing Sheets

(a)

(b)

(a)

(b)

(a)

(b)

(a)

(b)

(c)

(a)

(b)

BIODEGRADABLE NETWORK POLYMERS FOR REGENERATIVE MEDICINE AND TISSUE ENGINEERING

FIELD OF THE INVENTION

The present invention relates in general to biodegradable network polymers that are compatible with biological environments. In particular, the present invention relates to biodegradable polyether network polymers crosslinked via ester linkages, to substrates, implants and scaffolds comprising the biodegradable polyether network polymers, to methods for preparing such network polymers, implants and scaffolds, and to methods of using substrates, implants and scaffolds comprising the network polymers, particularly for culturing cells and regenerating tissue.

BACKGROUND

Polymer materials compatible with biological environments are of high interest due to their potential for use in a range of biomedical applications, such as tissue engineering. Polymer materials that have been investigated for use in such applications are generally of synthetic or natural origin.

Natural polymer materials such as collagen, alginate, chitosan and hydroxyapatite have been utilised in the preparation of scaffolds for tissue engineering applications targeting a variety of tissues. While such natural materials have many advantages, there are certain issues in regards to their use, such as batch-to-batch variation, risk of disease transmission and immunogenicity. In addition, processing methods required to obtain these natural materials can affect their physical properties. For example, even though collagen demonstrates high mechanical strength in vivo, the process of harvesting, isolation and purification significantly degrades this property due to the loss of natural cross-links.

Synthetic polymers on the other hand offer certain advantages over natural polymers. Such advantages can include a reduction in batch-to-batch variation, a higher degree of control over polymer structure, and the ability to tailor polymer composition and properties to suit particular applications.

Hydrophilic materials based on polyether polymers such as poly(ethylene glycol) (PEG) have been explored for biomedical applications. PEG in particular has been widely studied due to its water solubility, non-toxicity, minimal immunogenicity and anti-protein fouling properties, and has been approved by the US Food and Drug Administration (FDA) for use in drug and cosmetic applications. Various studies, in vitro and in vivo, have demonstrated the desirable biocompatibility of materials fabricated with PEG.

Crosslinked polymer network polymers and hydrogels based on polyethers such as PEG have been investigated for cell culture and tissue engineering applications, and various research groups have reported on the construction of PEG hydrogels using a variety of reaction conditions. However, while the PEG polymers and hydrogels are generally biocompatible, they are often not biodegradable.

Degradable PEG hydrogels have been prepared by incorporating polymer segments based on poly($\alpha$-hydroxy acids) such as poly(lactic acid) and poly(glycolic acid) into the hydrogel. However, a problem with the incorporation of poly($\alpha$-hydroxy acid) segments into the PEG hydrogel is that the poly($\alpha$-hydroxy acid) segments can be very hydrophobic, which can be a significant factor in inciting major foreign body responses. A further problem with poly($\alpha$-hydroxy acid) segments is that when they degrade, they can generate a high local concentration of acids, which can incite an inflammatory response.

It would be desirable to provide a biodegradable polyether network polymer that addresses or ameliorates one or more disadvantages or shortcomings associated with existing materials and/or to at least provide a useful alternative to such materials.

SUMMARY

In one aspect, the present invention provides a biodegradable polyether network polymer crosslinked via ester linkages which is prepared by polymerising a monomer composition comprising a multifunctional polyether monomer and a multifunctional crosslinking monomer, wherein one of the polyether monomer and the crosslinking monomer comprises a hydroxy functional group and the other of the polyether monomer and the crosslinking monomer comprises a complementary functional group capable of reacting with the hydroxy functional group to form an ester linkage, and wherein at least one selected from the polyether monomer and the crosslinking monomer is branched.

The polyether network polymer is crosslinked via ester linkages that are formed between a polyether monomer and a crosslinking monomer. The ester linkages are hydrolysable under physiological conditions and upon hydrolysis, allow degradation of the network polymer to occur.

In another aspect, the present invention provides a process for preparing a biodegradable polyether network polymer crosslinked via ester linkages, the process comprising the step of reacting a monomer composition comprising a multifunctional polyether monomer and a multifunctional crosslinking monomer under conditions allowing formation of ester linkages between the polyether monomer and the crosslinking monomer, wherein one of the polyether monomer and the crosslinking monomer comprises a hydroxy functional group and the other of the polyether monomer and the crosslinking monomer comprises a complementary functional group capable of reacting with the hydroxy functional group to form an ester linkage, and wherein at least one selected from the polyether monomer and the crosslinking monomer is branched.

In accordance with one or more aspects of the invention, one of the polyether monomer and the crosslinking monomer comprises a hydroxy functional group while the other of the polyether monomer and the crosslinking monomer comprises a complementary functional group that is capable of reacting with the hydroxy functional group to form an ester linkage. In one set of embodiments, the complementary functional group is selected from the group consisting of carboxylic acid, carboxylic acid ester, carboxylic acid anhydride and carboxylic acid halide. In a particular set of embodiments, the complementary functional group is a carboxylic acid halide.

To enable the polyether network polymer to be formed, at least one of the polyether monomer and the crosslinking monomer must be branched. In one embodiment, the polyether monomer is branched.

In embodiments of one or more aspects of the invention, the polyether monomer comprises a plurality of hydroxyl functional groups. In such embodiments, the crosslinking monomer therefore comprises the complementary functional group.

In some embodiments, the polyether monomer is branched and has a structure of formula (I):

$$A(BX)_n \qquad (I)$$

where:
  A is an n-valent core;
  B is a polyether segment;
  X is a hydroxy functional group; and
  n represents the number of (BX) groups and is at least 3.

In some embodiments, the polyether monomer employed in the preparation of the polyether network polymer comprises a polyether segment derived from a C2-C3 diol.

In one set of embodiments, each polyether segment in the polyether monomer has a molecular weight in a range selected from the group consisting of from about 100 to about 10,000 Da, from about 150 to about 5000 Da, and from about 200 to about 1000 Da.

In some embodiments, the polyether monomer is selected from the group consisting of glycerol ethoxylate and pentaerythritol ethoxylate.

In embodiments of one or more aspects of the invention, the crosslinking monomer comprises at least two complementary functional groups that are capable of reacting with hydroxy functional groups to form an ester linkage. In a particular set of embodiments, the crosslinking monomer comprises at least two carboxylic acid halide functional groups.

In one form, the crosslinking monomer may have a structure of formula (II):

$$R(Y)_m \quad (II)$$

where:
  R is a hydrocarbyl group;
  Y is a complementary functional group selected from the group consisting of carboxylic acid, carboxylic acid ester, carboxylic acid anhydride and carboxylic acid halide (preferably carboxylic acid halide functional group); and
  m represents the number of Y groups and is at least 2.

In some embodiments, crosslinking monomers of formula (II) may have a structure of formula (IIa) or (IIb):

(IIa)

(IIb)

where:
  R is a hydrocarbyl group; and
  Y is a complementary functional group selected from the group consisting of carboxylic acid, carboxylic acid ester, carboxylic acid anhydride and carboxylic acid halide (preferably carboxylic acid halide).

In embodiments of the crosslinking monomer of formulae (II), (IIa) and (IIb), R may be a linear, branched, cyclic or aryl hydrocarbyl group. In some specific embodiments, R may comprise from 2 to 12 carbon atoms.

In one form, the crosslinking monomer may be selected from the group consisting of succinyl chloride, adipoyl chloride, sebacoyl chloride, glutaroyl chloride, pimeloyl chloride, suberoyl chloride and trimesoyl chloride, preferably succinyl chloride and sebacoyl chloride.

The monomer composition used to prepare the biodegradable polyether network polymer may comprise a molar ratio of polyether monomer to crosslinking monomer in a range selected from the group consisting of from about 5:1 to 1:5, or from about 3:1 to 1:3. In one set of embodiments, the molar ratio of polyether monomer to crosslinking monomer is about 1:2.

In one set of embodiments, the monomer composition used in the preparation of the biodegradable polyether network polymer may further comprise a mechanical property modifier. In some embodiments, the monomer composition may comprise up to 20% (w/w), up to 15% (w/w), or up to 10% (w/w) of mechanical property modifier. The mechanical property modifier may be a hydrophobic macromolecule or a hydrophobic oligomer.

When the mechanical property modifier is a hydrophobic macromolecule, the macromolecule may be a polyester polyol, such as for example, dihydroxy poly(caprolactone).

In one set of embodiments, the biodegradable polyether network polymer of the present invention is porous. In such embodiments, the biodegradable polyether network polymer may have an average pore diameter in the range of from about 1 nm to about 3 mm.

In one form, reaction between the polyether monomer and the crosslinking monomer generates a condensate in gaseous form that produces pores in the polyether network polymer.

In one set of embodiments, the monomer composition used in the preparation of the biodegradable polyether network polymer may further comprise a solid porogen, such as for example, porogen particles. The porogen particles may have a particle size in a range selected from the group consisting of from about 50-1000 μm, about 100-700 μm and about 300-600 μm. In some embodiments the porogen particles may comprise salt particles.

The biodegradable polyether network polymer of the invention may be used in a range of applications.

In one aspect there is provided an in vitro cell culture substrate comprising a biodegradable polyether network polymer according to any one of the embodiments described herein. In one form, the cell culture substrate is in the form of a film.

In another aspect there is provided an implantable device comprising a substrate comprising a biodegradable polyether network polymer according to any one of the embodiments described herein, and cells seeded on to the substrate.

In another aspect there is provided a scaffold comprising a biodegradable polyether network polymer according to any one of the embodiments described herein. In some embodiments the scaffold is in the form of a porous sponge.

In another aspect of the present invention there is provided a process for preparing a porous biodegradable polyether network polymer crosslinked via ester linkages, the process comprising the step of reacting a monomer composition comprising a multifunctional polyether monomer and a multifunctional crosslinking monomer under conditions allowing formation of a polyether network polymer crosslinked via ester linkages and the generation of a gaseous condensate in situ that produces a plurality of pores within the network polymer, wherein one of the polyether monomer and the crosslinking monomer comprises a hydroxy functional group and the other of the polyether monomer and the crosslinking monomer comprises a complementary functional group capable of reacting with the hydroxy functional group to form an ester linkage, wherein at least one selected from the polyether monomer and the crosslinking monomer is branched.

The present invention further provides a method of regenerating tissue in a subject, the method comprising the step of implanting a scaffold comprising a biodegradable polyether network polymer according any one of the embodiments described herein in a desired site in the subject. In one set of embodiments the tissue is adipose tissue and the scaffold is implanted in the breast area of the subject.

The present invention further provides a method of culturing cells comprising the step of contacting cells with a substrate comprising a biodegradable polyether network polymer according to any one of the embodiments described herein under conditions of cell culture.

The present invention further provides a method of preparing an implantable device comprising the steps of providing a substrate comprising a biodegradable polyether network polymer according to any one of the embodiments described herein and seeding the substrate with cells. In one form, the device is an ocular implant for implantation in an eye of a subject and the cells are selected from the group consisting of corneal epithelial cells and corneal endothelial cells.

The present invention further provides a method for the treatment of a disorder or condition in a subject comprising the steps of providing an implantable device comprising a substrate comprising a biodegradable polyether network polymer according to one or more embodiments described herein and cells seeded on the substrate, and implanting the device in a site in the subject where treatment is desired. In some embodiments, the disease or disorder is corneal endothelial dysfunction and the method comprises the step of implanting a device comprising corneal endothelial cells seeded on a substrate comprising a biodegradable polyether network polymer according to one or more embodiments described herein in an eye of a subject.

BRIEF DESCRIPTION OF THE DRAWINGS

Preferred embodiments of the invention will herein be illustrated by way of example only with reference to the accompanying drawings in which.

DETAILED DESCRIPTION

Figure 1:
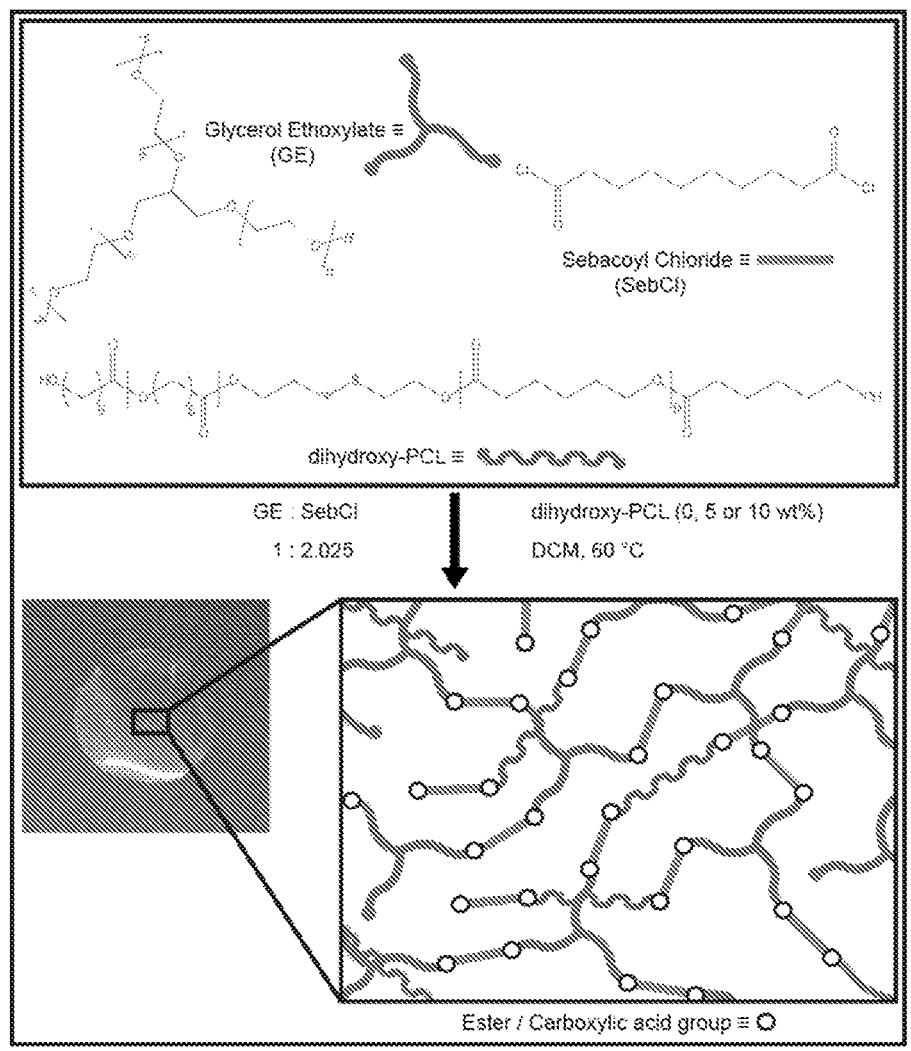
FIG. 1 is a scheme illustrating the synthesis of a biodegradable polyether network polymer via reaction of glycerol ethoxylate (GE), sebacoyl chloride (SebCl) and dihydroxy PCL in accordance with one embodiment of the invention.

The present invention relates to a biodegradable polyether network polymer crosslinked via ester linkages and to processes for preparing these network polymers. The ester linkages contained in the polyether network polymer are biodegradable and are hydrolytically and/or enzymatically cleavable in a biological environment, allowing for breakdown of the crosslinked network polymer. Degradation products resulting from breakdown of the network polymer are substantially non-toxic to the body.

The terms "degradable" and "biodegradable" as used herein in relation to a substance, linkage or group means that the substance, linkage or group is susceptible to degradation, cleavage or fragmentation over time under physiological conditions or in a biological environment. Such degradation, cleavage or fragmentation may occur via chemical decomposition (e.g. via hydrolysis or reduction) of suitably labile moieties under selected physiological or biological conditions. When used in relation to a polymer substance, the terms "degradable" and "biodegradable" indicate that the polymer comprises suitably labile or degradable moieties as part of the molecular structure of the polymer. The cleavage or breakdown of one or more degradable moieties in the polymer leads to fragmentation of the polymer, generally into monomers and/or lower molecular weight polymer fragments.

In one aspect, the present invention provides a biodegradable polyether network polymer crosslinked via ester linkages which is prepared by polymerising a monomer composition comprising a multifunctional polyether monomer and a multifunctional crosslinking monomer, wherein one of the polyether monomer and the crosslinking monomer comprises a hydroxy functional group and the other of the polyether monomer and the crosslinking monomer comprises a complementary functional group capable of reacting with the hydroxy functional group to form an ester linkage, and wherein at least one selected from the polyether monomer and the crosslinking monomer is branched.

To form the biodegradable polyether network polymer, a monomer composition comprising a multifunctional polyether monomer and a multifunctional crosslinking monomer is employed. The polyether monomer and the crosslinking monomer present in the monomer composition each comprise functional groups that are capable of covalently reacting in order to polymerise and form the biodegradable polyether network polymer. The polyether network polymer that results from the polymerisation reaction is a solid and insoluble polymer matrix.

At least one of the polyether monomer and the crosslinking monomer contained in the monomer composition is branched. In some embodiments the polyether monomer is branched. In other embodiments the crosslinking monomer is branched. When one monomer is branched, the other monomer may be linear or branched.

In some embodiments, the polyether monomer is branched, with a degree of branching of at least 3. In such embodiments, the crosslinking monomer may be linear or branched. In one set of embodiments where the polyether monomer is branched, the crosslinking monomer is linear.

The polyether monomer and crosslinking monomer contained in the monomer composition are multifunctional, with each of the monomers comprising a plurality of functional groups. A monomer that is multifunctional comprises two or more functional groups. When a monomer is branched however, that monomer will generally comprise at least 3 functional groups.

In accordance with the invention, one of the polyether monomer and the crosslinking monomer comprises hydroxy functional groups, while the other of the polyether monomer and the crosslinking monomer comprises complementary functional groups that are capable of reacting with the hydroxy functional groups to form ester linkages.

As used herein, the term "linkage" refers to a group that is formed as a result of a covalent chemical reaction between two complementary functional groups.

The complementary functional group that reacts with the hydroxy groups may be selected from the group consisting of carboxylic acid, carboxylic acid ester, carboxylic acid anhydride and carboxylic acid halide functional groups. In one set of embodiments, the complementary functional groups are carboxylic acid halide groups.

As will be explained further below, the use of monomers comprising hydroxy functional groups and carboxylic acid halide functional groups in the preparation of the biodegradable polyether network polymer can be advantageous, as the condensate produced from the covalent reaction of such monomers may assist in the generation of porous network polymer structure.

In one set of embodiments the monomer composition comprises a polyether monomer comprising a plurality of hydroxy functional groups. The number of functional groups present in the polyether monomer may be dependent on whether the polyether monomer is linear or branched. In one set of embodiments, the polyether monomer is a linear polyether polyol, a branched polyether polyol, or a mixture thereof.

In one set of embodiments the monomer composition comprises a linear polyether monomer comprising two hydroxy functional groups. Such linear polyether monomers may be referred to herein as linear polyether diols. The linear polyether monomer may comprise a polyether segment that may be derived from a C2-C3 diol. Suitable linear polyether monomers include poly(ethylene glycol) and poly(propylene glycol), as shown by the following general equations:

where p and q represent the number of repeating ethylene oxide or propylene oxide units, respectively.

Linear polyether diols present in the monomer composition may have a molecular weight in a range selected from the group consisting of from about 100 to 10,000 Da, from about 150 to 5000 Da, and from about 200 to 1000 Da.

In one set of embodiments the monomer composition may comprise a branched polyether monomer comprising at least three hydroxy functional groups. In such embodiments, the polyether monomer may have a structure of formula (I):

$$A(BX)_n \quad (I)$$

where:
A is an n-valent core;
B is a polyether segment;
X is a hydroxy functional group; and
n represents the number of (BX) groups and is at least 3.

In formula (I), A represents a central n-valent core moiety that is suitable for making a branched polyether monomer. In some embodiments, the polyether monomer may be a star-shaped, where multiple arms radiate from a central core. In such embodiments, A represents the core of the star, with the arms of the star represented by the group (BX).

The degree of branching of the polyether monomer (represented by n) can be varied by varying the nature of the core moiety A. Different degrees of branching may be used to control the mechanical and physical properties of the polyether network polymer. In some embodiments of formula (I), n is an integer selected from the group consisting of 3, 4, 6 and 8.

In some embodiments of formula (I), A may be derived from a multivalent compound selected from the group consisting of glycerol, glycerol oligomers, pentaerythritol, pentaerythritol oligomers, sorbitol, trimethyloylpropane and di(trimethyloylpropane).

In formula (I), B represents a polyether segment of the polyether monomer. The polyether segment may be derived from a C2-C3 diol. In particular embodiments, each polyether segment comprises poly(ethylene glycol) (PEG).

Where the monomer of formula (I) is star-shaped, each arm of the star may comprise a polyether segment having a molecular weight in a range selected from the group consisting of from about 100 to 10,000 Da, from about 150 to 5000 Da, and from about 200 to 1000 Da. In some embodiments, each polyether segment comprises poly(ethylene glycol) having a molecular weight in a range selected from the aforementioned. The molecular weight of the polyether segment will dictate the length of the arms and may influence some of the physical properties of the resulting polyether network polymer, such as for example, water compatibility or hydrophilicity.

Polyether monomers comprising poly(ethylene glycol) (PEG) segments may be advantageous in some embodiments as poly(ethylene glycol) is biocompatible, hydrophilic, non-toxic and non-immunogenic. Polymer fragments resulting from the breakdown of the network polymer which comprise PEG may also be readily cleared from the body through normal excretory pathways.

In one set of embodiments, the monomer composition may comprise a branched polyether monomer selected from the group consisting of glycerol ethoxylate and pentaerythritol ethoxylate.

A biodegradable polyether network polymer prepared with a polyether monomer comprising PEG may be regarded as a biodegradable poly(ethylene glycol) network polymer.

When the monomer composition comprises a polyether monomer comprising a plurality of hydroxy functional groups, the crosslinking monomer that is also present in the monomer composition comprises a plurality of functional groups that are complementary to the hydroxy functional groups of the polyether monomer. The complementary functional groups are capable of reacting with the hydroxy functional groups to form ester linkages.

In some embodiments, the crosslinking monomer may comprise a plurality of complementary functional groups selected from the group consisting of carboxylic acid, carboxylic acid ester, carboxylic acid anhydride and carboxylic acid halide functional groups. In one set of embodiments, the crosslinking monomer comprises at least two carboxylic acid halide functional groups.

When the polyether monomer is branched, the crosslinking monomer may be linear or branched.

When the polyether monomer is linear, such as for example, a linear polyether diol, the crosslinking monomer must be branched.

In one set of embodiments the crosslinking monomer has a structure of formula (II):

$$R(Y)_m \quad (II)$$

where:
R is a hydrocarbyl group;
Y is a complementary functional group selected from the group consisting of carboxylic acid, carboxylic acid ester, carboxylic acid anhydride and carboxylic acid halide (preferably carboxylic acid halide); and
m represents the number of Y groups and is at least 2.

The crosslinking monomer comprises at least two complementary functional groups and in formula (II), the number of complementary functional groups is represented by the group m. In formula (II), m is at least 2 and in some embodiments, m may be 3 or more.

In some embodiments, a crosslinking monomer of formula (II) may have a structure of formula (IIa) or (IIb), where m is 2 or 3 in formula (II):

In monomers of formula (IIa) and (IIb), R and Y may be selected from the groups defined herein for formula (II).

In one form, the complementary functional group represented by Y in the crosslinking monomer of formulae (II), (IIa) or (IIb) may be a carboxylic acid halide functional group at each occurrence. When Y is a carboxylic acid halide functional group, the halide moiety of the functional group may be selected from any one of those that is conventionally used. In some embodiments, the halide moiety of the carboxylic acid halide functional group may be selected from the group consisting of fluoride, chloride, bromide, and iodide, preferably chloride and bromide. In one form, the carboxylic acid halide functional group may be a carboxylic acid chloride or a carboxylic acid bromide functional group.

The hydrocarbyl group R present in the crosslinking monomer of formulae (II), (IIa) and (IIb) may be selected from the group consisting of a linear, branched, cyclic or aryl hydrocarbyl group. In some embodiments, R is a linear, branched, cyclic or aryl hydrocarbyl group comprising from 2 to 12 carbon atoms. In some embodiments, R is a linear, branched, cyclic or aryl hydrocarbyl group comprising from 8 to 12 carbon atoms. Such groups may in some embodiments be considered to be hydrophobic hydrocarbyl groups.

In embodiments of the invention, the monomer composition used to prepare the biodegradable polyether network polymer may comprise a crosslinking monomer selected from the group consisting of succinyl chloride, adipoyl chloride, sebacoyl chloride, glutaroyl chloride, pimeloyl chloride, suberoyl chloride, trimesoyl chloride, and combinations thereof. The choice of crosslinking monomer may be used to control the swelling extent, degradation rate and mechanical properties of the polyether network polymer. For example, a crosslinking monomer comprising a hydrophobic hydrocarbyl group may be employed to reduce the water swellability and improve the tensile properties of the polymer network by balancing hydrophilic properties provided by the polyether monomer.

In some embodiments it may be advantageous for the monomer composition to comprise a crosslinking monomer selected from succinyl chloride and sebacoyl chloride. The use of monomers such as succinyl chloride and sebacoyl chloride may be beneficial as such monomers are capable of being converted into succinic acid and sebacic acid in a biological environment upon breakdown of the network polymer. Succinic acid and sebacic acid are biocompatible and minimally toxic. For example, sebacic acid is a dicarboxylic acid that naturally occurs in cells and is an intermediate in fatty acid oxidation, while succinic acid is an intermediate in the Kreb's/citric acid cycle.

The monomer composition employed in the preparation of the biodegradable polyether network polymer may comprise any suitable quantity of polyether monomer and crosslinking monomer. In some embodiments, the monomer composition may comprise a molar ratio of polyether monomer to crosslinking monomer in the range of from about 5:1 to 1:5 or from about 3:1 to 1:3. In one embodiment, the molar ratio of polyether monomer to crosslinking monomer in the monomer composition is about 1:2. It can be desirable to have an excess of crosslinking monomer to ensure that a sufficient number of crosslinks are formed, particularly if a linear crosslinking monomer is used.

In one set of embodiments, the monomer composition used to prepare the biodegradable polyether network polymer may further comprise a mechanical property modifier. The mechanical property modifier is used to help control the mechanical properties of the polyether network polymer, such as tensile properties. The mechanical properties of materials intended for use in regenerative medicine and tissue engineering applications can be important to promote desirable cellular and tissue interactions and to ensure the mechanical integrity of an implant.

The mechanical property modifier may be present in the monomer composition in an amount selected from the group consisting of up to 20% (w/w), up to 15% (w/w) and up to about 10% (w/w).

In some embodiments, the mechanical property modifier may be hydrophobic macromolecule, such as a hydrophobic polymer or a hydrophobic oligomer. A hydrophobic oligomer will generally comprise fewer monomer repeat units than a hydrophobic polymer. For example, the hydrophobic oligomer may comprise no more than 10 monomer repeat units. It is preferable that the hydrophobic macromolecule be biocompatible and minimally toxic to a biological environment.

A hydrophobic macromolecule may be stiffer than the polyether network polymer, which may be generally hydrophilic. The inclusion of the hydrophobic macromolecule can therefore modify the mechanical properties of the network polymer.

The hydrophobic macromolecule may also modify the swellability of the generally hydrophilic polyether network polymer in an aqueous environment. Water swellability of the network polymer may be measured as an equilibrium swelling ratio (% ESR), which is calculated according to Equation (1):

$$\% \ ESR = ((W_s - W_d)/W_d) \times 100\% \quad (1)$$

where $W_s$ and $W_d$ refers to the swollen and dried weights of the network polymer respectively.

The inclusion of a hydrophobic macromolecule can limit the % ESR obtained for the polyether network polymer. In some embodiments, it can be advantageous for the polyether network polymer to exhibit minimal swelling (low % ESR) as this could ensure there any implant prepared using the polyether network polymer would exhibit a minimal change in physical dimensions upon exposure to an aqueous biological environment.

In one set of embodiments, the hydrophobic molecule employed as a mechanical property modifier is biodegradable and comprises functional groups that are capable of degrading in a biological environment. By this is meant that the hydrophobic macromolecule may be susceptible to hydrolytic and/or enzymatic cleavage and the like in a biological environment, leading the ability of the macromolecule to break down to lower molecular weight degradation products in the biological environment. In one set of embodiments, the mechanical property modifier is a hydrophobic molecule comprising at least one functional group selected from the group consisting of ester, amide, urethane (carbamate) and disulfide functional groups, and mixtures thereof.

In one set of embodiments the hydrophobic macromolecule may be a hydrophobic polyester polyol. An exemplary hydrophobic polyester polyol is dihydroxy poly(caprolactone). As the polyester polyol comprises hydroxy functional groups, the polyester polyol is capable of covalently reacting with the monomer that comprises the complementary functional groups, thus leading to covalent incorporation of the polyester polyol as a component of the polyther network polymer. Furthermore, the ester groups in the polyester polyol may be susceptible to hydrolytic or enzymatic cleavage, thereby allowing the hydrophobic macromolecule to be removed through the production of low molecular weight fragments as the network polymer degrades. In one set of embodiments, the polyester polyol may also comprise disulfide groups. The disulfide groups may be susceptible to reduction or enzymatic cleavage in a biological environment and may facilitate degradation of the polyester polyol.

In one set of embodiments, the biodegradable polyether network polymer may comprise a polyester polyol in an amount selected from the group consisting of from 0 to 20% (w/w), from 0.1% to 15% (w/w), and from about 0.5% to 10% (w/w). In one embodiment, the polyester polyol is dihydroxy poly(caprolactone).

The biodegradable polyether network polymer may be prepared in a one-step reaction whereby a mixture comprising the multifunctional polyether monomer and the multifunctional crosslinking monomer is formed, then the mixture of monomers is allowed to covalently react for a time sufficient to form the polyether network polymer.

In another aspect the present invention provides a process for preparing a biodegradable polyether network polymer crosslinked via ester linkages, the process comprising the step of reacting a monomer composition comprising a multifunctional polyether monomer and a multifunctional crosslinking monomer under conditions allowing formation of ester linkages between the polyether monomer and the crosslinking monomer, wherein one of the polyether monomer and the crosslinking monomer comprises a hydroxy functional group and the other of the polyether monomer and the crosslinking monomer comprises a complementary functional group capable of reacting with the hydroxy functional group to form an ester linkage, and wherein at least one selected from the polyether monomer and the crosslinking monomer is branched.

The monomer composition may comprise a polyether monomer and crosslinking monomer selected from any one of those described herein.

The monomer composition may also further comprise a mechanical property modifier as described herein.

In some embodiments, the monomer composition comprises a solvent. The solvent may be an organic solvent. The solvent may assist to solubilise the polyether monomer and the crosslinking monomer, so that a homogeneous monomer composition can be obtained. This may be useful as polyether monomers such a glycerol ethoxylate and pentaerythritol ethoxylate are water soluble, while crosslinking monomers such as dicarboxylic acid halides are water insoluble. As a result, difficulties may be encountered in mixing the monomers together in the absence of added solvent. In other embodiments, the monomer composition is free of added solvent.

One skilled in the art would understand that the covalent reaction between a hydroxy functional group and a complementary functional group will generally produce a condensate. The condensate is generally a small molecule that is eliminated as a by-product of the covalent reaction between the functional groups.

In one embodiment the complementary functional group is a carboxylic acid chloride, and reaction between the carboxylic acid chloride with a hydroxy functional group produces hydrochloric acid (HCl) as a condensate. One advantage of the use of carboxylic acid chloride-hydroxy chemistry to form the polyether network polymer is that in addition to the reaction producing biodegradable ester linkages, the reaction also proceeds relatively quickly and with high efficiency, reducing the need to employ coupling agents or other additives as might be used in prior art processes to promote polymer formation. Furthermore, the carboxylic acid chloride-hydroxy reaction does not need special reaction conditions (such as an oxygen-free environment), which might be required for network polymers formed by radical polymerisation.

The process for preparing the biodegradable polyether network polymer may be carried out at room temperature or at elevated temperature. The reaction between the polyether monomer and the crosslinking monomer may be exothermic, resulting in an increase in temperature as the reaction between the monomers proceeds and the polyether network polymer is formed. Reaction between the monomers may promote the generation of a condensate in gaseous form. For example, reaction between monomers comprising a carboxylic acid chloride functional group and a hydroxy functional group can generate hydrochloric acid in gaseous form. The gaseous condensate produces pores in the polyether network polymer.

In one set of the embodiments, the biodegradable polyether network polymer may be porous, with pores having an average pore diameter in the range of from about 1 nm to about 3 mm. In some embodiments, the biodegradable polyether network polymer may have a structure comprising interconnected pores.

The pores may be produced as a result of the network polymer forming around bubbles of gaseous condensate that is generated in situ during polymerisation of the monomer composition. It is an advantage that the in situ generated gas can eliminate the need to use agents such as surfactants in order to generate a porous structure comprising pores that are large enough to allow nutrient transfer and to support cellular growth, tissue penetration and vascularisation.

Pores may also be produced in the polyether network polymer through the use of a porogen. Accordingly, in some embodiments where a porous biodegradable polyether network polymer is desired, the monomer composition used to prepare the polymer may further comprise a solid porogen. The covalent reaction of the polyether monomer with the crosslinking monomer therefore occurs in the presence of the porogen so as to form the porous polyether network polymer. The porous network polymer is obtained after removal of the porogen. It can be an advantage to employ a porogen to form a porous network polymer as the porogen will provide greater control over the pore sizes produced in the network polymer.

In one embodiment the monomer composition further comprises porogen particles. The particles may have a particle size in a range selected from the group consisting of from about 50 to 1000 µm, from about 100 to 700 µm, or from about 300 to 600 µm. In some embodiments, the porogen particles are water soluble. In one embodiment the porogen particles are salt particles. The salt particles will generally comprise a suitable a salt, such as sodium chloride. The salt particles may be fused salt particles, which may be formed in a humid atmosphere. One advantage of the use of fused salt particles is that they can form water soluble porogen particles of large particle size (for example, approximately 100-700 µm). The fused salt particle may also help in the formation of interconnecting pores in the polyether network polymer.

The porogen particles may be subsequently removed after polymer formation to give a porous crosslinked polyether network polymer. The porogen particles may be removed by introducing an appropriate solvent to the network polymer then allowing the porogen to dissolve in the solvent and thereby leach out of the polymer. Where the porogen particles are water soluble, water may be used as the solvent for removal of the particles. As the polyether network polymer is a three-dimensional crosslinked macromolecular structure, it is not soluble in the solvent.

The biodegradable polyether network polymer is a three-dimensional crosslinked macromolecular structure that is generally insoluble in a range of solvents. In some embodiments, the biodegradable polyether network polymer may be capable of swelling in a selected solvent. In some embodiments, the biodegradable polyether network polymer is capable of swelling in an aqueous solvent. This may occur due to the hydrophilic nature of the polyether monomer employed in the preparation of the network polymer and/or the porosity of the network polymer. Upon swelling in an aqueous solvent, the network polymer may resemble a gel. Accordingly, in such embodiments, the biodegradable polyether network polymer may be considered to be a hydrogel.

The pore size of the porous network polymer can have an influence on mechanical properties. Various process conditions can produce porous biodegradable polyether network polymers with different moduli. The possibility to tailor the compressive moduli of the porous network polymers by varying porosity would allow the mechanical properties of the network polymers, and the properties of implantable devices and scaffolds prepared with the network polymers, to be adjusted to suit a range of tissue types, such as adipose, kidney, prostate tissue and cardiac muscle.

The biodegradable polyether network polymer of the invention may be used in a range of applications.

In one aspect there is provided an in vitro cell culture substrate comprising a biodegradable polyether network polymer according to any one of the embodiments described herein. In one form, the cell culture substrate is in the form of a film. The film may be a nanoporous film, having pores with a pore diameter in the nanometer range. A nanoporous film will allow the transfer of nutrients and fluids required to support cell growth.

In another aspect there is provided an implantable device comprising a substrate comprising a biodegradable polyether network polymer according to any one of the embodiments described herein, and cells seeded on to the substrate.

If desired, the implantable device may also comprise growth factors and/or other biological and chemical entities that facilitate the growth or proliferation of specific types of cells.

In one form, the implantable device is an ophthalmic device for implantation in an eye of a subject and the cells are selected from the group consisting of corneal epithelial cells and corneal endothelial cells.

Thus in some embodiments the present invention provides an ocular implant comprising a substrate comprising a biodegradable polyether network polymer according to any one of the embodiments described herein and cells selected from the group consisting of corneal epithelial cells and corneal endothelial cells seeded on the substrate.

The substrate of the ocular implant preferably has greater than 98% transparency to visible light and may be in the form of a film. In one form the substrate may be in the form of a nanoporous film. The substrate may be of a suitable thickness that facilitates manipulation of the device and implantation of the device in a desired site in an eye of a subject. The thickness of the substrate may be adjusted by altering the quantity of monomers present in the monomer composition used to prepare the biodegradable polyether network polymer. In one set of embodiments, the substrate has a thickness in the range of from about 10 to 150 µm when in a hydrated state. It is an advantage of the biodegradable polyether network polymer of the invention that the mechanical properties of the network polymer are such that it is possible to prepare relatively thin films with the network polymer. This can be of benefit when the films are used as substrates in implantable devices, as it can facilitate the use of minimally invasive surgical procedures.

In another aspect there is provided a scaffold comprising a biodegradable polyether network polymer according to any one of the embodiments described herein. In some embodiments the scaffold is in the form of a porous sponge as described herein. As discussed further below, the scaffold may be employed in tissue engineering applications, particularly soft tissue engineering.

In another aspect of the present invention there is provided a process for preparing a porous biodegradable polyether network polymer crosslinked via ester linkages, the process comprising the step of reacting a monomer composition comprising a multifunctional polyether monomer and a multifunctional crosslinking monomer under conditions allowing formation of a polyether network polymer crosslinked via ester linkages and the generation of a gaseous condensate in situ that produces a plurality of pores within the network polymer, wherein one of the polyether monomer and the crosslinking monomer comprises a hydroxy functional group and the other of the polyether monomer and the crosslinking monomer comprises a complementary functional group capable of reacting with the hydroxy functional group to form an ester linkage, and wherein at least one selected from the polyether monomer and the crosslinking monomer is branched.

In one form the above process, the in situ generated gaseous condensate expands the polyether network polymer as it forms, thereby resulting in foaming of the network polymer. The expanded porous polyether network polymer may, in one form, resemble or be a porous sponge. The polymer sponge is biodegradable and crosslinked as a result of the ester linkages formed between the polyether monomer and the crosslinking monomer.

In one set of embodiments of the process for preparing a porous biodegradable polyether network polymer, the monomer composition containing the polyether monomer and the crosslinking monomer is reacted in a vessel of finite void volume. A vessel of finite void volume may be a closed reaction vessel. Reaction of the monomers in a vessel of finite void volume might influence pore size or structure. For example, reaction of the monomer composition in a vessel with a larger finite void volume will generate larger pores in the porous polyether network polymer, compared to when the same monomer composition is reacted in a vessel of smaller finite void volume. The difference in pore size is thought to be related to pressures in the vessel resulting from the in situ generation of the gaseous condensate. Similar changes in pore size can also be obtained by varying the quantity of monomers in the monomer composition.

In other embodiments of the process for preparing a porous biodegradable polyether network polymer, the monomer composition is reacted in a vessel of infinite void volume. For example, the monomer composition may be allowed to react in an open vessel. In this instance, the resulting porous polyether network polymer will have a large pore size.

Reaction of the polyether monomer and the crosslinking monomer in the monomer composition may proceed at room temperature or elevated temperature.

The monomer composition employed in the preparation of the porous biodegradable polyether network polymer may comprise a polyether monomer and a crosslinking monomer of any one of the embodiments described herein.

In one form, the polyether monomer comprises a plurality of hydroxy functional groups and the crosslinking monomer comprises a plurality of carboxylic acid halide functional groups.

In a specific form, the polyether monomer comprises a plurality of hydroxy functional groups and the crosslinking monomer comprises a plurality of carboxylic acid chloride functional groups. In such an embodiment, the gaseous condensate that is generated in situ when the hydroxy and carboxylic acid chloride functional groups react to form the ester linkages would be gaseous hydrochloric acid (HCl).

In some embodiments, the monomer composition employed in the preparation of the porous biodegradable polyether network polymer may further comprise a mechanical property modifier as described herein. In one set of embodiments, the monomer composition may comprise a mechanical property modifier in an amount selected from the group consisting of up to 20% (w/w), up to 15% (w/w), and up to 10% (w/w).

The mechanical property modifier may be a hydrophobic macromolecule. An exemplary hydrophobic macromolecule is a polyester polyol, such as dihydroxy poly(caprolactone). In one set of embodiments, the monomer composition may comprise a polyester polyol in an amount selected from the group consisting of from 0 to 20% (w/w), from 0.1% to 15% (w/w), and from about 0.5% to 10% (w/w).

In some embodiments, the monomer composition employed in the preparation of the porous biodegradable polyether network polymer may further comprise a porogen, such as porogen particles as described herein. In one embodiment the porogen particles are salt particles, for example fused salt particles. The porogen may have a particle size in a range selected from the group consisting of from about 50 to 1000 µm, from about 100 to 700 µm, or from about 300 to 600 µm. The porogen may help to produce larger pores and/or help to control the size and structure of the pores generated in the polyether network polymer.

The biodegradable porous polyether network polymer may have an interconnected porous structure, which is formed in situ as a result of the reaction between the polyether monomer and the crosslinking monomer and the gaseous condensate produced from the reaction. If the monomer composition used to prepare the porous network polymer comprises a porogen, an interconnected porous structure having large pores may be produced.

An interconnected porous structure comprising large pores with interconnecting channels may be advantageous for tissue engineering applications. The large pores would allow tissue and vascularisation to penetrate, and facilitate the proliferation and development of tissue. Furthermore, interconnecting channels can provide the means for cellular migration, tissue expansion and formation of vascular systems within the porous structure. The innerconnected nature of the porous structure would also allow for nutrient and fluid transport as well as the clearance of cellular waste products.

The polyether network polymer described herein is suitable for use in a range of applications where a biocompatible and biodegradable polymer is desired.

The biodegradable polyether network polymer demonstrates excellent mechanical and degradation properties with non-toxicity and minimal immunogenicity in vitro and in vivo. These characteristics ultimately enable the network polymers to be excellent candidates for use as scaffolds in tissue engineering applications and as substrate for cell culture and implantable devices. The biodegradability of the polyether network polymer means that any foreign material would not accumulate at the implantation site, thus allowing the surrounding tissue to revert to its native structure.

The present invention further provides a method of regenerating tissue in a subject, the method comprising the step of implanting a scaffold comprising a biodegradable polyether network polymer according any one of the embodiments described herein in a desired site in the subject. In one set of embodiments the tissue is adipose tissue and the scaffold is implanted in the breast area of the subject. The scaffold can be used in reconstructive or cosmetic procedures where the regeneration of tissue is desired.

The present invention further provides a method of culturing cells comprising the step of contacting cells with a substrate comprising a biodegradable polyether network polymer according to any one of the embodiments described herein under conditions of cell culture. The method may be used with any proliferative cell that is capable of proliferating in cell culture. In one set of embodiments of the method, the cells are selected from the group consisting of endothelial cells and epithelial cells, in particular, corneal endothelial cells and corneal epithelial cells.

The present invention further provides a method of preparing an implantable device comprising the steps of providing a substrate comprising a biodegradable polyether network polymer according to any one of the embodiments described herein and seeding the substrate with cells. In one form, the device is an implantable ophthalmic device for implantation in an eye of a subject and the cells are selected from the group consisting of corneal epithelial cells and corneal endothelial cells.

The present invention further provides a method for the treatment of a disorder or condition in a subject comprising the steps of providing an implantable device comprising a substrate comprising a biodegradable polyether network polymer according to one or more embodiments described herein and cells seeded on the substrate, and implanting the device in a site in the subject where treatment is desired. In some embodiments, the disease or disorder is corneal endothelial dysfunction and the method comprises the step of implanting an ocular implant in an eye of a subject, wherein the ocular implant comprises a substrate comprising a biodegradable polyether network polymer according to one or more embodiments described herein and corneal endothelial cells seeded on the substrate. The inventors have observed that corneal transparency is advantageously able to be maintained over several weeks with the ocular implant.

The polyether network polymer of the invention is capable of degrading in a biological environment, and producing non-toxic degradation by-products. The rate of biodegradation may vary from days to weeks, and can be adjusted by varying the quantity of labile ester linkages in the polyether network polymer. In some embodiments, degradation of the polyether network polymer can occur in a time period of from about 2 weeks to about 20 weeks.

In some embodiments the biodegradability of the polyether network polymer may be modified by adjusting the morphology of the network polymer. For example, a polyether network polymer in the form of a porous sponge may exhibit faster degradation rates due to the porous structure of the polymer providing a larger surface area that can be exposed to a biological environment.

The biodegradable polyether network polymers of the invention are synthetic polymers that have been found to be biocompatible, non-toxic and minimally immunogenic. The ability to control the degradability, mechanical properties and permeability of the network polymers enable these polymers to be fabricated into versatile substrates and scaffolds for regenerative medicine and tissue engineering applications.

The following examples are intended to illustrate the scope of the invention and to enable reproduction and comparison. They are not intended to limit the scope of the disclosure in any way.

Examples

Biodegradable Poly(Ethylene Glycol) (PEG) Films
Materials

Glycerol ethoxylate ($M_n$~1 kDa), sebacoyl chloride (≥95%), phosphate buffered saline (PBS) tablets, ε-caprolactone (97%), 2,2'-dithiodiethanol (90%), stannous octoate (~95%), toluene (anhydrous, 99.8%), Costar Ultra-low attachment plates, insulin, transferrin, selenium, 4',6-diamidino-2-phenylindole (DAPI) fluorescent stain, Triton X-100, and dextran $M_r$ ~500000, glucose assay kit (Sigma GAGO-20: glucose oxidase/peroxidise reagent and O-dianisidine dihydrochloride) and albumin-fluorescein isothiocyanate conjugate from bovine (albumin-FITC) were obtained from Sigma-Aldrich and used as received. Dulbecco's Modified Eagle Medium (DMEM), Fetal Bovine Serum (FBS), L-glutamine, trypsin-EDTA (0.05%), trypan blue (0.4%) and penicillin-streptomycin were obtained from GIBCO. DMEM was supplemented with 10% v/v FBS, 1% v/v L-glutamine and 1% v/v penicillin-streptomycin prior to use for the cell viability assays. NUNC T225, canted neck flasks were obtained from Thermo Fisher Scientific. Thermanox tissue culture plastic (TCP) coverslips was obtained from NUNC. Dulbecco's Modified Eagle Medium:Nutrient Mixture F12 (DMEM:F12), antibiotic-antimycotic, epidermal growth factor (EGF), fetal calf serum (FCS), Alexa Fluor 488 goat anti mouse IgG, trypsin, and EDTA was obtained from Invitrogen. Anti-Na+/K+ ATPase (β2-subunit) monoclonal IgG produced in mouse clone M17-P5-F11 was obtained from Santa Cruz Biotechnology. Matrix assisted laser desorption/ionisation time-of-flight mass spectroscopy (MALDI ToF MS) matrix trans-2-[3-(4-tert-butylphenyl)-2-methyl-2-propenylidene]malononitrile (DCTB) (≥99.0) and cationisation agent (NaTFA (99.999%)) were purchased from Aldrich and used as received. Tetrahydrofuran (THF) (Honeywell, 99.99%), D-glucose (99.5 dichloromethane (99.5%) were supplied by Chem-Supply and used as received. CelltiterAqueousOne solution for cell viability assays was obtained from Promega and used as received.

Synthesis of α,ω-Dihydroxyl Polycaprolactone (Mechanical Property Modifier)

α,ω-Dihydroxyl polycaprolactone (dihydroxyl PCL) was prepared via ring-opening polymerisation (ROP) of ε-Caprolactone. ε-Caprolactone (20.0 g, 175 mmol), 2,2'-dithiodiethanol (1.08 g, 7.00 mmol) and stannous octoate (0.95 g, 2.34 mmol) were dissolved in anhydrous toluene (45 mL) and heated at 110° C. under argon for 24 h. The mixture was cooled to room temperature, diluted with THF (50 mL) and precipitated into cold methanol (−18° C., 1 L). The precipitate was collected by filtration and dried in vacuo (0.1 mbar) to afford α,ω-dihydroxyl PCL as a white powder, 18.8 g (94%); $M_n$ (NMR)=3.2 kDa, (MALDI ToF)=3.3 kDa (PDI=1.07).

Preparation of Biodegradable PEG Films

A desired amount of dihydroxyl PCL (5 or 10 wt % PCL content, respectively) was dissolved in dichloromethane (DCM) (15 mL). Glycerol ethoxylate (0.70 mmol) and sebacoyl chloride (1.42 mmol) were added to the dihydroxyl PCL solution, which was mixed thoroughly and allowed to stand at room temperature for 1 h with occasional agitation. A sample with no PCL was also prepared. The monomer solutions used to prepare the PEG films are detailed in Table 1.

TABLE 1

| Example No | Glycerol Ethoxylate (mL) | Sebacoyl Chloride (mL) | Dihydroxy PCL (g) | PCL content (wt %) |
|---|---|---|---|---|
| 1 | 0.62 | 0.30 | 0.0 | 0 |
| 2 | 0.62 | 0.30 | 0.052 | 5 |
| 3 | 0.62 | 0.30 | 0.104 | 10 |

A volume (7.5 mL) of each of the above monomer solutions was pipetted onto a glass petri dish (diameter 10 cm). Each dish was then placed in a vacuum oven at 60° C. for 20 min prior to the application of vacuum (20 mbar). After a further 30 min the dish was removed and allowed to cool to room temperature. The circumference of the film was scored with a scalpel and the petri dish was filled with deionised water (20 mL). After 15 min the water was removed and 1:1 THF:deionised water (40 mL) was added. The film was detached from the petri dish surface and placed in water (250 mL). The water was changed with fresh water every 15 min (3×250 mL) and the films were dried under vacuum for 24 h (20 mbar, 30° C.). The dried films were stored in a desiccator until further use.

Environmental scanning electron microscopy (EnviroSEM) and spectral reflectance analysis were used to determine the thickness of the cross-linked PEG films. Hydrated films were determined to have an average thickness of approximately 50 μm.

As a result of the small thickness of the films and the casting conditions (20 mbar, 60° C.) the volatile solvent dichloromethane and formed HCl gas are readily removed during the casting process. Subsequent washing and swelling of the hydrogel film with water was conducted to ensure complete removal of HCl. Replacement of the water with tetrahydrofuran (THF) allows solvent exchange within the film between water and THF, and the resulting swelling allows the film to easily detach from the petri dish surface, which in a dry state is not achievable without damaging the cast film.

Equilibrium Swelling Ratio and Contact Angle Measurements

To observe the swelling characteristics, the PEG films prepared above were allowed to swell in 1×PBS for 24 h. The equilibrium swelling ratio (% ESR) of the various films was calculated using the equation % ESR=$((W_s-W_d)/W_d)\times$ 100%, where $W_s$ and $W_d$ refer to the swollen and dried weights, respectively. The analysis was conducted in triplicate for each type of film and the results averaged.

Water contact angle measurements were carried out with Data Physics OCA 20 Tensiometer. Measurements were recorded with OCA software, using the sessile drop technique (10 μL droplet) on completely swollen films with 0, 5, and 10 wt % PCL contents. Measurements were taken 60 s after the water droplets were placed onto the surfaces of the films.

The results of the above experiments are shown in Table 2.

TABLE 2

| Sample | PCL content (%) | % ESR | Contact angle (deg) |
|---|---|---|---|
| Example 1 | 0 | 118 ± 4 | 44 ± 0.4 |
| Example 2 | 5 | 109 ± 5 | 58 ± 0.7 |
| Example 3 | 10 | 100 ± 4 | 67 ± 0.4 |

As shown in Table 2, it was found that with increasing PCL contents (0, 5 and 10 wt %), the % ESR of the films decreased slightly (118, 109, 100%, respectively). This is the result of water repelling effect of the hydrophobic PCL component reducing the swelling capabilities of the PEG films. Increasing PCL content also led to an increase in contact angles from 44° to 58° and 67° respectively, indicating a slight increase in the hydrophobicity of the PEG films.

Light Transmittance Evaluation

Hydrated PEG films were placed in 1×PBS solution for 1 h and then subjected to UV-Vis evaluation. The transmittance of the films was recorded at 25° C., over the UV and visible spectrum (290-750 nm). The results revealed that the PEG films containing 0%, 5% and 10% PCL are able to transmit >98% of visible light at all wavelengths (400-700 nm).

Tensile Evaluation

Tensile testing was performed to determine the tensile capabilities of the PEG films prepared with various amounts of PCL (0, 5 and 10 wt %) and allow comparison with the human cornea (Table 3). Dehydrated films were swollen in 1×PBS and cut into dog-bone shapes with 2×2 cm gage area and 2 cm tabs for the evaluation of their tensile properties. The films were clamped between wooden tabs within the metal clamps of the Instron Microtester to prevent slippage and jaw tearing of the films. The films were not stress preconditioned prior to tensile testing. Tensile evaluation of the films was carried out in the temperature controlled water bath of the microtester in 1×PBS solution at 35° C. A minimum of three repeats of each type of film (with 0, 5 or 10 wt % PCL) were tested. The clamped samples were stretched at a rate of 0.1 mm/s with a 50 N load cell, until breakage of the films in the gage area occurred. Any film that did not break within the gage area was disregarded for compilation of raw data. Data obtained from the Bluehill software was exported into OriginPro 7.5 software for graphing and determination of key parameters such as ultimate tensile stress/strain and tensile modulus. The results are summarised in Table 3.

TABLE 3

| Sample | PCL content (wt %) | Ultimate stress (MPa) | Ultimate Strain % | Tensile Modulus (MPa) |
|---|---|---|---|---|
| Example 1 (0% PCL) | 0 | 1.5 ± 0.2 | 33 ± 5.0 | 3.3 ± 0.6 |
| Example 2 (5% PCL) | 5 | 3.7 ± 0.7 | 71 ± 17 | 3.8 ± 0.8 |
| Example 3 (10% PCL) | 10 | 5.2 ± 0.2 | 61 ± 3.0 | 6.3 ± 0.8 |
| Human Cornea | — | 3.3 ± 0.2 | 60 ± 15 | 15.9 ± 2.0 |
| Descemet's Membrane | — | 0.3 ± 0.01 | 1.7 ± 0.2 | 2.6 ± 0.4 |

It has been shown from the above results that addition of hydrophobic PCL can improve the mechanical properties of resultant PEG films. Additionally, PEG films with 0 and 5 wt % PCL content demonstrate a comparable tensile modulus to that of the Descemet's Membrane, which may be of assistance when developing an implantable device for the regeneration of corneal endothelial cells.

In Vitro Degradation Studies

Figure 2:
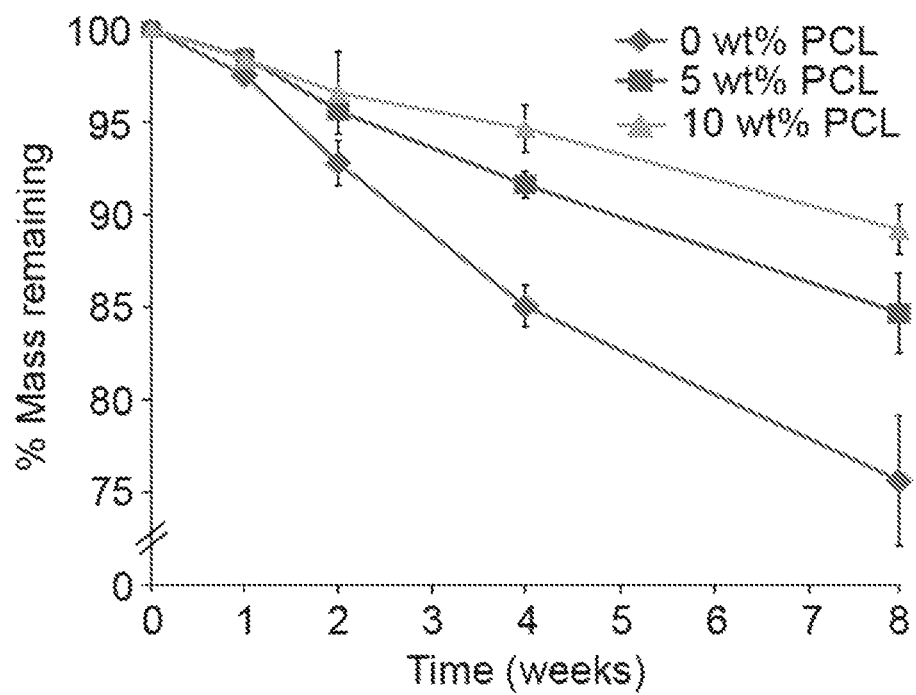
FIG. 2 shows a graph illustrating the in vitro degradation profile over 8 weeks of biodegradable polyether network polymers with different quantities of mechanical property modifier (PCL) in accordance with embodiments of the invention.

Hydrated films with 0, 5 and 10% PCL content were cut into 2×2 cm squares. After three washes with water (20 mL) at 5 min intervals, the films were dried in vacuo (20 mbar) at 40° C. for 24 h. The dried films were weighed, transferred to vials (28 mL) and 1×PBS (20 mL) was added. Subsequently, the containers were placed in a temperature controlled orbital shaker at 35° C., the natural temperature of the corneal anterior chamber. Three containers with films were removed from the orbital shaker at time points of 1, 2, 4 and 8 weeks. The removed films were washed with water (3×20 mL) for 15 min with occasional gentle agitation and were dried in vacuo (20 mbar) for 24 h at 40° C. The dried films were weighed and the masses were plotted against time to obtain a degradation profile of the films. Calculation of the degree of degradation of the films with 0%, 5% and 10% PCL content revealed mass losses of ~24%, 15% and 10%, respectively, in 8 weeks. The results are shown in FIG. 2.

In Vitro Permeability Evaluation of PEG Films

Glucose and albumin diffusivity measurements were carried out in a side-by-side diffusion cell (PermeGear, Bethlehem, Pa.) with 5 mL cell volumes. The films (5 wt % PCL) were placed between the diffusion cells and tightly clamped to prevent leakage. For glucose measurements one cell (source) was filled with glucose in PBS (0.05 g/mL, 4 mL) and the other cell (target) with PBS buffer only (4 mL). For albumin measurements, albumin-fluorescein isothiocyanate conjugate (albumin-FITC) in PBS (50 µM, 4 mL) was placed in the source cell and PBS buffer was placed in the target cell. For both glucose and albumin measurements the chambers were maintained at 35° C. with magnetic stirring in each cell. At set times (30, 45, 60, 80 and 100 min) aliquots (2 mL) were removed from the target cell and replaced with fresh PBS (2 mL). For glucose measurements, samples were prepared for spectrophotometric analysis using a glucose assay kit (Sigma GAGO-20: glucose oxidase/peroxidise reagent and O-dianisidine dihydrochloride reagent) and analysed using a Shimadzu UV-1800 spectrophotometer at 540 nm. For albumin measurements, the absorbance of the albumin-FITC at 495 nm was measured using a Shimadzu UV-1800 spectrophotometer.

The in vitro permeability studies showed the film with 5% PCL had diffusivities of 2.3 (±0.3)×10$^{-6}$ and 1.0 (±0.2)×10$^{-7}$ cm$^2$/s for glucose and albumin, respectively. In comparison, literature reports suggest the human cornea has diffusivities for glucose and albumin of 2.6 (±0.3)×10$^{-6}$ and 1.0×10$^{-7}$ cm$^2$/s, respectively (see Rafat M, Li F, Fagerholm P, Lagali N S, Watsky M A, Munger R, Matsuura T, Griffith M. PEG-stabilised carbodiimide crosslinked collagen-chitosan hydrogels for corneal tissue engineering. Biomaterials 2008; 29:3960-3972). The in vitro diffusivity study demonstrates that PEG films are permeable to both large and small molecules that are important for the survival and function of tissue, such as the human cornea.

In Vitro Cytotoxicity Evaluation of PEG Films

To assess the cytotoxicity of the films, dehydrated films (5 wt % PCL, 100 mg) were placed in 80% v/v ethanol solution for 30 min. The films were then washed and rehydrated with sterile PBS (3×20 mL) at intervals of 10 min. The rehydrated films were subsequently placed in sterile supplemented DMEM (2 mL) and subsequently incubated at 37° C. for 72 hours. The films were removed from the solution and the conditioned media was used in the cell viability assay. To investigate the effects of film degradation products on cell viability, dehydrated films (500 mg) were degraded in 1 M HCl (5 mL) over 30 min. The solution was concentrated in vacuo and the residue was azeotroped with water (5×20 mL) and then dried in vacuo (0.1 mbar). The degradation products (100 mg) were dissolved in sterile DMEM (2 mL). The solutions were then sterilised under UV for 30 min and filtered through 0.22 µm nylon filters prior to use in the toxicity studies. NIH 3T3-L1 cells were grown to confluence in T225 flasks in supplemented DMEM at 37° C. in 5% CO$_2$ atmosphere with 95-100% humidity. Cells were trypsinised using 0.05% Trypsin-EDTA (GIBCO), counted manually using trypan blue as live/dead stain, diluted with fresh medium to afford a seeding density of 1.25×10$^5$ cells/mL and plated onto 96 well plates (80 µL/well). Some wells were left blank to serve as cell-blank controls. The plates were returned to the incubator for 4 h prior to the addition of the films conditioned media and films degradation product solutions. The prepared stock solutions (50 mg/mL) were twice diluted by a factor of 10 using fresh complete medium. 20 µL of the stock solution and the two dilutions thereof were added to the 96 well plates in triplicate (to obtain concentrations of 100, 1000 and 10000 ppm), gently mixed by orbital movement of the plates and then the plates were returned to the incubator for a further 72 h incubation. Subsequently, CelltiterAqueousOne solution was added to the plates (20 µL/well), the plates were gently rocked to facilitate mixing and then returned to the incubator for 30 min to 4 h. In periodic intervals the UV-Vis absorbance of the plates was read at 490 nm and 700 nm using a Cary 50 Bio UV-Visible Spectrophotometer equipped with a micro plate reader. The colour of the solutions equilibrated after ca. 2 h incubation. Absorbance values at 490 nm were corrected for background absorbance (700 nm) and absorbance of the medium alone (cell-blank controls), and then normalised to the growth control.

Figure 3:
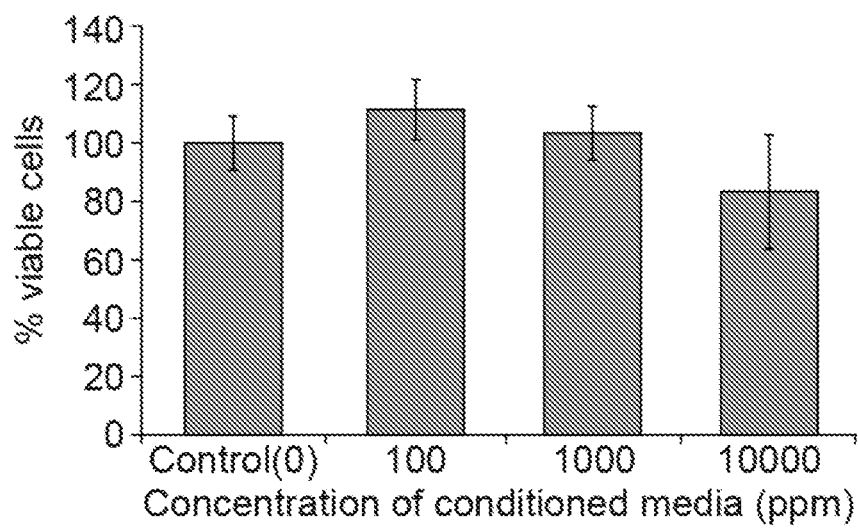
FIG. 3 shows graphs illustrating the results of a cytotoxicity evaluation of (a) polymer conditioned media and (b) degradation products of biodegradable polyether network polymers containing different quantities of PCL in accordance with embodiments of the invention.
Figure 3:
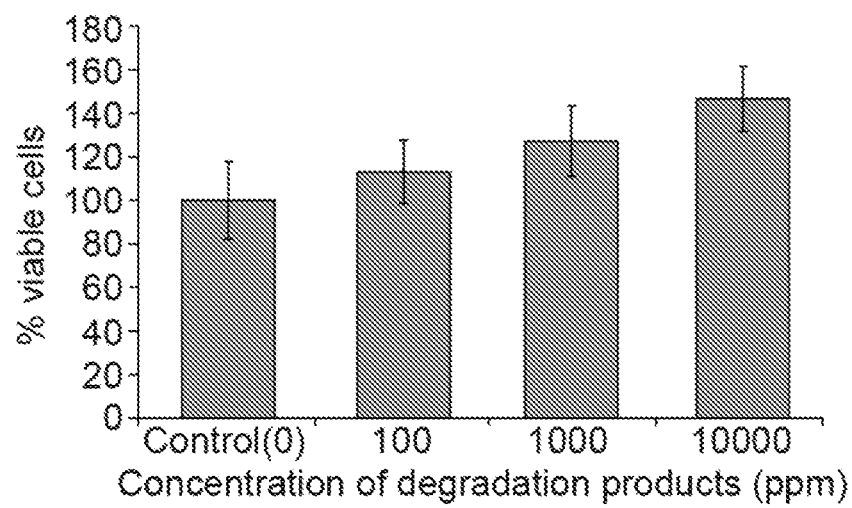

After the incubation of cells for 72 h in the presence of various concentrations (100, 1000 and 10000 ppm) of PEG film conditioned media and the degradation products, minimal toxicity was observed, as seen in FIGS. 3(a) and (b).

In the presence of the degradation products (obtained via accelerated acid catalysed hydrolysis) the cells remained viable and metabolically active relative to the control (no degradation products), even at the extremely high concentrations of 10000 ppm (FIG. 3(b)). Degradation of the PEG film via the hydrolysis of ester linkages yields low toxicity compounds such as PEG, sebacic acid and 6-hydroxyhexanoic acid (from degradation of the PCL).

With regards to the PEG film conditioned media, no negative effect on the viability and metabolic activity of cells was observed at concentrations of 100 and 1000 ppm. Although a slight decrease in the metabolic activity of the cells was observed at the very high concentration of 10000 ppm (FIG. 3(a)) the standard deviation of this data is well within the range of the control data and can be considered statistically negligible. The results of the cytotoxicity studies suggest that the PEG films and their degradation products do not impair cell growth and are benign, making them suitable platforms for tissue regeneration and as implantable substrates.

Corneal Endothelial Cell (CEC) Harvesting and In Vitro Cell Seeding of PEG Film Substrates Dehydrated films (5 wt % PCL) were rehydrated in PBS (20 mL) and cut into circular disks (diameter 16 mm) using a circular hole puncher. Subsequently, the films were placed in 80% v/v ethanol (20 mL) for 1 h. The films were then washed with sterile PBS solution (3×20 mL) at intervals of 15 min. The films were then placed into a 24 well plate with sterile glass rings (external diameter 15 mm) placed on top of the films. PBS (2 mL) was added into wells containing the films and the well plate was stored at 8° C. in a refrigerator prior to cell culture studies. Neither surface modification nor protein conjugation was carried out on the films prior to cell culture studies.

Ovine corneal endothelial cells (CEC's) were selected for in vitro cell seeding studies. Eye orbs from fresh scavenged experimental cadavers of merino sheep, were washed with proviodine (1:50, 8 min), methanol (20% v/v, 60 s), peracetic acid (0.1% v/v, 5 min), and in PBS with antibiotic-antimycotic. Corneas were then dissected and transferred to thinning media (1:1 DMEM:F12, insulin (0.5 µg/mL), transferrin (0.275 µg/mL), selenium (0.25 ng/mL), EGF, 2% FCS, antibiotic-antimycotic and dextran) for 16 h. Descemet's membrane was dissected from corneal tissues, treated with collagenase (2 mg/mL) for 60 min, and trypsin (0.05%)-EDTA (0.02%) for 5 min. Descemet's membrane in the samples was then cut into small pieces and triturated to produce a single cell suspension, subsequently the decellularised Descemet's fragments were removed. 50000 cells were seeded onto films or Thermanox tissue culture plastic (TCP) coverslips in corneal media (1:1 DMEM:F12, insulin 0.5 µg/mL, transferrin 0.275 µg/mL, selenium 0.25 ng/mL, EGF, 10% FCS, and antibiotic-antimycotic). Cell culture was performed under standard conditions (37° C., 5% $CO_2$).

For immunofluorescence studies, Descemet's membranes dissected from sheep corneas were used as positive controls. Test samples were cultured sheep CECs on films. All samples were fixed with 4% paraformaldehyde (PFA) for 10 min before washing in PBS and stored at 4° C. until use. Immunofluorescence was performed as follows. Samples were permeabilised with 0.3% Triton X-100 for 15 min before washing with PBS. Blocking was with 3 normal goat serum for 30 min. Samples were incubated with the primary antibody (Anti-Na+/K+ATPase IgG antibody) in PBS for 2 h in a humidified chamber. The negative controls were incubated without a primary antibody. After PBS washing the samples were incubated with the secondary antibody for 1 h (Alexa Fluor 488). After PBS washing samples were incubated with 4',6-diamidino-2-phenylindole (DAPI) for 5 min. After a final PBS wash, samples were mounted with aqueous medium. Images were obtained using an Olympus BX61.

Computer Assisted Stereographic Tomography (CAST, Olympus) was used to determine cell density from haematoxylin labelled nuclei. For comparison the cell density of freshly dissected ovine corneas was determined by phase contrast microscopy (Lions Eye Donation Service, CERA).

In Vitro CEC Attachment and Proliferation on Substrates with PEG Films

Figure 4:
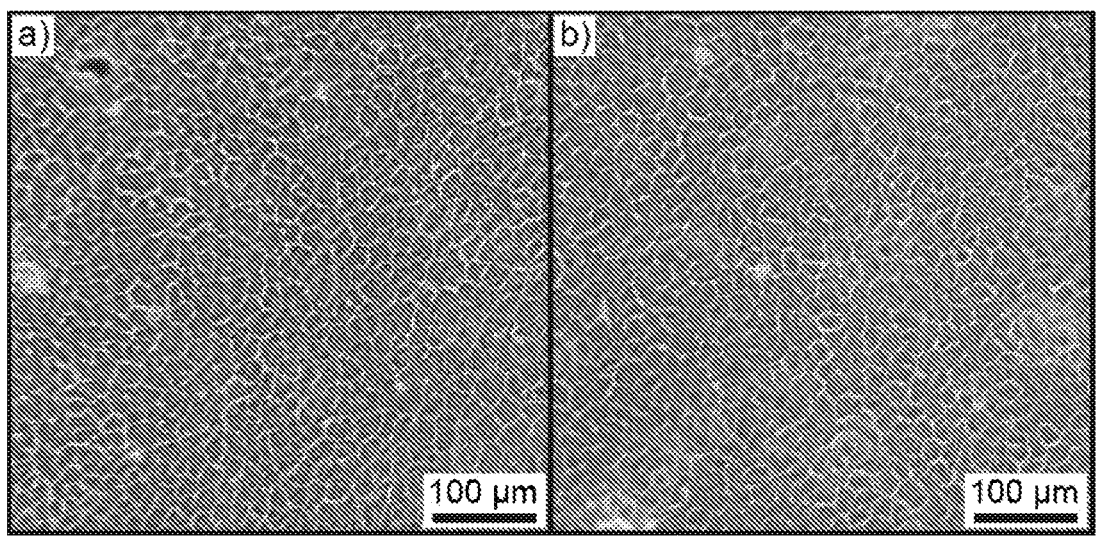
FIG. 4 shows (a) a microscopy image of sheep corneal endothelial cells (CECs) cultured on tissue culture plate, and (b) microscopy image of CECs cultured on a biodegradable polyether network polymer with 5 wt % PCL in accordance with one embodiment of the invention.

The cultured CECs retained their natural in vivo polygonal morphology, as seen in FIGS. 4 (a) and (b). CAST counting of cells cultured on the PEG film substrates gave a cell density of 3150 cell/mm$^2$ (std error=459, n=4). This cell density is identical to that of sheep CEC in vivo, 3150 cells/mm$^2$ (std error=88, n=3) determined by specular microscopy. Immunofluorescence demonstrates that cultured cells are positive to Na+K+ATPase. Na+K+ATPase is a regulator of pump function and has been used as a marker for CECs. Observation of Na+K+-ATPase at the lateral periphery of CECs is indicative of intact pump function. Sheep CECs readily proliferated on the PEG film substrates. The PEG films were capable of supporting CEC attachment and proliferation without the conjugation of any adhesion ligands such as collagen or RGD. Cells cultured on the films provided a cell density of 3150 cell/mm$^2$ (SEM 459, n=4) compared to a density of 3150 cell/mm$^2$ (SEM 88, n=3) in corneas from 14 month old merino sheep. These cell densities are comparable to those of healthy human corneas and sufficient for eye donation service quality control standards (generally >2500 cell/mm$^2$).

In Vivo Toxicity and Immune Response Evaluation

Hydrated films (5 wt % PCL) were cut into disks (10 mm diameter) using a hole puncher, dried at 40° C. for 24 h and then sealed in double sample bags. The films were sterilised at a minimum dose of 25 kGy at Steritech (Dandenong, Victoria, Australia). The sterilised films were used for the evaluation of in vivo toxicity and immune response of the films.

All procedures were conducted according to the guidelines of the National Health and Medical Research Council (NHMRC) of Australia and were approved by Faculty of Veterinary Science Animal Ethics Committee, The University of Melbourne. Merino sheep (n=4) were fasted for 24 h prior to surgical procedure. The pupil of the eye to be operated on was dilated with one drop of topical 1% atropine sulphate and one drop of 10% viscous phenylephrine hydrochloride 1 h prior to the procedure. Anaesthesia was induced with 25 mg/kg sodium thiopentone intravenously into the external carotid vein, and maintained after intubation of the airway with 1.5% halothane in 2:1 air/oxygen. A 3 mm slit was made into the cornea via an ophthalmic slit knife and the films were inserted using fine forceps. The incision made into the anterior chamber prior to the film insertion was sutured and the sheep were allowed to recover.

Following surgery, the corneal morphology was examined using a hand-held slit-lamp every 2-3 days and scored for clarity, oedema and indices of inflammation, using a validated proforma. Specifically, clarity and oedema were each scored on a scale of 0-4, with 0 being completely transparent (for clarity) or thin (for oedema), and 4 being completely opaque (for clarity) or maximally thick (for oedema).

28 days after implantation, the sheep were euthanised via intrajugular lethabarb injection and the eye orbs were harvested. For end-point histology, tissues were fixed in buffered formalin, embedded in paraffin wax, cut at 5 µm and stained with haematoxylin and eosin (H&E). Sections were examined to determine immune reactions, degradation of the films, maintenance of the CEC monolayer and any blockage of the trabecular meshwork.

Results:

The PEG films with 5 wt % used for the in vivo implantation study maintained their integrity during the procedure, and their elastic properties allowed facile handling throughout the surgery.

Over the 28 day slit-lamp observation, the test (PEG film—denoted PHF) corneas maintained their optical transparency and no significant differences were noted visually in comparison to the control corneas (with no PEG film). No evidence of oedema or opacity was observed. Macroscopically no adverse effects could be discerned via the slit-lamp observations. In order to determine if any negative effects were caused in a microscopic level, histological analysis was conducted.

Figure 5:
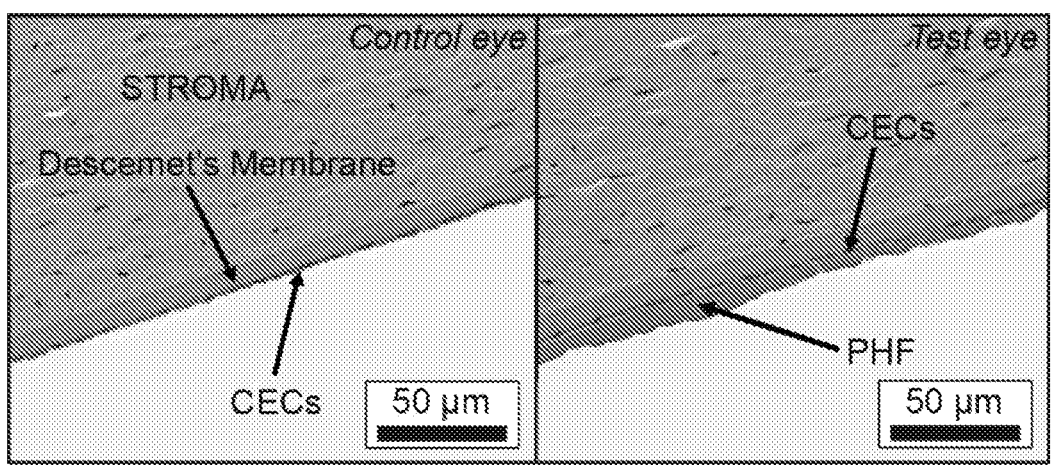
FIG. 5 shows microscopy images of H&E stained sections of (a) control, and (b) biodegradable polyether network polymer (PHF) implanted sheep cornea after 28 days implantation.

The ovine orbs were harvested at 28 days following implantation and prepared for histological evaluation. Following sectioning and staining with haematoxylin & eosin (H&E), histological analysis of the control and test corneas revealed the natural morphology of the stroma, Descemet's membrane and the corneal endothelium (FIG. 5). It was also observed that the PEG films had adhered onto the interior surface of the cornea in some regions, with no toxicity. The adherence of the PEG films onto the interior corneal surface on top of the CECs did not compromise native CEC function as the cornea maintained its optical transparency throughout the study. This is advantageous since adhesion of the film is necessary for the CECs to be able to pump across the films and the cornea to maintain corneal transparency. It is also useful for surgical purposes as its adhesion will make it easier for the surgeon to maintain the implant in place.

In Vivo Safety Testing of Tissue Engineered Corneal Endothelium (TECE) in an Ovine Model As part of a series of pilot experiments to establish the surgical method a single animal was implanted with a tissue engineered corneal endothelium (TECE) (a PEG carrier film with a cultured allogenic ovine corneal endothelial cell (OCEC) monolayer) without first removing the endogenous OCEC and maintained for 51 days (51 d). The cornea remained clear and oedema free. There was no evidence of toxicity or immune rejection at 51 d. Histology failed to find the polymer film within the orb indicating that it had completely biodegraded by 51 d.

Establishing an Ovine Model of CEC Loss and Treatment by TECE Implantation

An ovine model of corneal endothelial cell loss was established by manually stripping the corneal endothelium. TECE were able to be implanted using a DSEAK-like procedure. The TECE had sufficient tensile strength for ease of implantation and readily unfolded smooth and flat against the posterior surface of the cornea. DMEK donors scroll tightly and are difficult to unroll and place flat against the posterior surface of the cornea. Animals with experimental corneal endothelial loss without a TECE present placed over the wound had non-healing corneal oedema. Where the TECE was placed over the wounded region oedema abated. Slight opacity to small regions of the cornea of test animals due to stromal scarring (observation and confirmed by histology in one case). In an animal maintained for 62 d after surgery histology found no trace of the PEG film within the orb confirming that the film completely degrades within the anterior chamber.

Porous Biodegradable Poly(Ethylene Glycol) (PEG) Sponge Materials

Pentaerythritol ethoxylate ($M_n$ ~797 Da), sebacoyl chloride (≥95%) and phosphate buffered saline (PBS) tablets were obtained from Sigma-Aldrich and were used as received. Dulbecco's Modified Eagle Medium (DMEM), Fetal Bovine Serum (FBS), L-glutamine, trypsin-EDTA (0.05%), trypan blue (0.4%) and penicillin-streptomycin were obtained from GIBCO. DMEM was supplemented with 10% v/v FBS, 1% v/v L-glutamine and 1% v/v penicillin-streptomycin prior to use for the cell viability assays. NUNC T225, canted neck flasks were obtained from Thermo Fisher Scientific. Dichloromethane (≥99.5%), ethanol (undenatured 100%), sodium carbonate (≥99.2%, anhydrous) were obtained from Chem-Supply and were used as received. Selleys Quick Fix Supa Glue (ethyl cyanoacrylate/poly(methyl methacrylate)) was obtained from Woolworths, Australia. CelltiterAqueousOne solution for cell viability assays was obtained from Promega and used as received.

Preparation of Porous Biodegradable PEG Sponge

Pentaerythritol ethoxylate (PE) and sebacoyl chloride (SebCl) were pipetted into polyethylene vials (28 mL total volume) in a 1:2 mole ratio (amounts shown in Table 4).

For Examples 4 to 7, the volume of PE and SebCl (monomer volume) were varied to obtain different precursor occupied volumes (% POV); represented as a percentage of the total container volume. For Examples 8 to 11, the monomer volume remained constant, but various amounts of dichloromethane (DCM) were added to vary the % POV. The lids were then secured tightly and the vials were immediately vortexed for 15 s before being placed inside a fume cupboard. After a further 60 s the lids were removed and the vials were left in the fume cupboard for 15 min. Example 12 is identical to Example 6, however the lid removed after vortexing.

The resulting sponges were removed from the vials and the non-uniform sections at the bottom were removed with a scalpel. Subsequently, the sponges were placed in a 30 mM sodium carbonate solution (100 mL/sponge) for 1 h to neutralise any HCl, followed by soaking in deionised water for 30 min (3×200 mL). The sponges were dehydrated by soaking in ethanol for 20 min (2×100 mL), dried in vacuo (30° C., 20 mbar) for 24 h and then stored in a desiccator until further use.

TABLE 4

| Ex. No | PE Vol (mL) | PE Moles (mmol) | SebCl Vol (mL) | SebCl Moles (mmol) | DCM (v/v %) | Void vol (%) | Precursor vol (mL) |
|---|---|---|---|---|---|---|---|
| 4 | 4.87 | 7.33 | 3.13 | 14.7 | — | 71.5 | 8 |
| 5 | 3.65 | 5.50 | 2.35 | 11.0 | — | 78.6 | 6 |
| 6 | 2.44 | 3.67 | 1.57 | 7.33 | — | 85.7 | 4 |
| 7 | 1.22 | 1.83 | 0.78 | 3.67 | — | 92.9 | 2 |
| 8 | 2.31 | 3.48 | 1.49 | 6.97 | 5 | 85.7 | 4 |
| 9 | 2.19 | 3.30 | 1.41 | 6.60 | 10 | 85.7 | 4 |
| 10 | 1.95 | 2.93 | 1.25 | 5.87 | 20 | 85.7 | 4 |
| 11 | 1.22 | 1.83 | 0.78 | 3.67 | 50 | 85.7 | 4 |
| 12* | 2.44 | 3.67 | 1.57 | 7.33 | — | — | 4 |

*Lid was removed immediately after vortexing.

Figure 6:
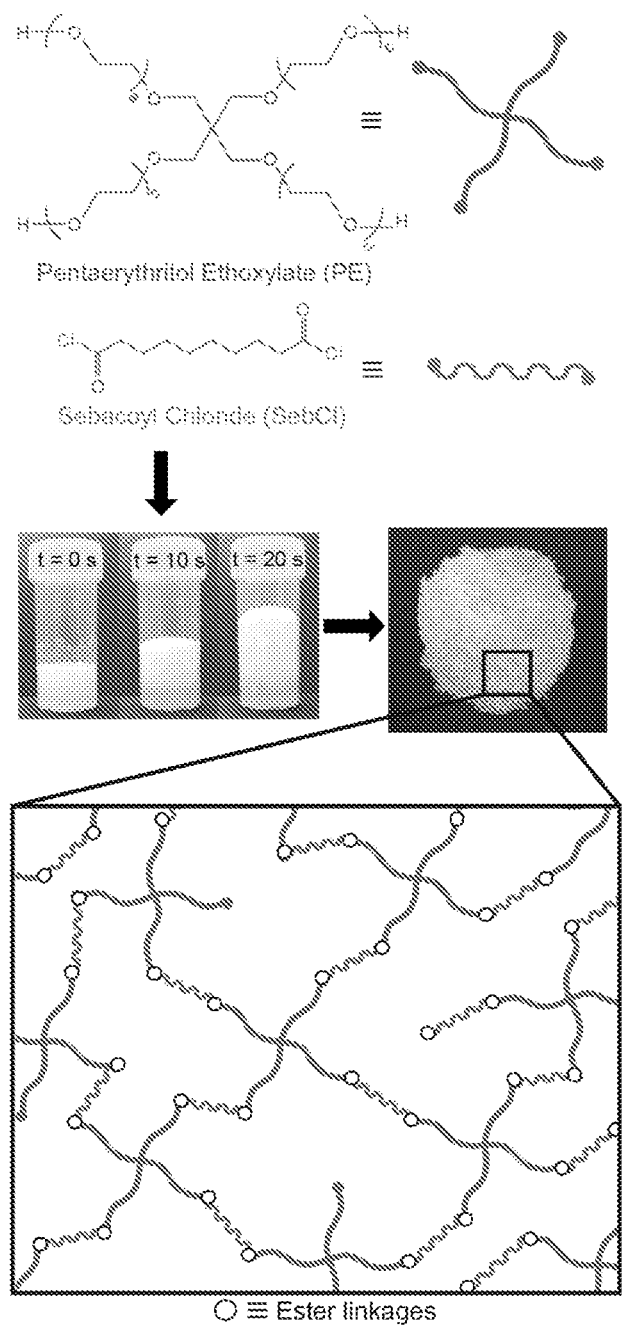
FIG. 6 is a scheme illustrating the fabrication of biodegradable porous PEG sponges using pentaerythritol ethoxylate (PE) and sebacoyl chloride (SebCl) in accordance with one embodiment of the invention.

Reaction between pentaerythritol ethoxylate (PE) and sebacoyl chloride (SebCl) under restricted volume conditions in sealed containers resulted in the formation of porous poly(ethylene glycol) sponges. The reaction between the acid chloride groups of the SebCl cross-linker and the hydroxyl end-groups of PE led to the formation of ester linkages and the simultaneous release of hydrogen chloride (HCl) gas. The reaction is exothermic and releases HCl as a gas very rapidly. The combined generation of HCl gas and increase in the solution viscosity as a result of the rapid cross-linking reaction between PE and SebCl leads to foaming of the mixture, with gelling taking place within 20 s following vortexing (FIG. 6). The cross-linking and gel formation traps the gas bubbles in place producing an interconnected porous network.

SEM Evaluation of Porous Structure

The porous PEG sponges were cut in half and mounted on carbon tabs. The exposed internal surfaces were analysed using a FEI Quanta FEG 200 E-SEM under low vacuum conditions to observe the porous structure of the sponges. ImageJ (National Health Institute, USA) software was utilised to determine the average pore sizes. Results are shown in Table 5.

TABLE 5

Average pore and channel size of porous PEG sponges

| Example No | Pore size (μm) | Channel size (μm) |
|---|---|---|
| 4 | 571 ± 205 | 222 ± 81 |
| 5 | 908 ± 209 | 302 ± 90 |
| 6 | 1000 ± 433 | 445 ± 182 |
| 7 | 1387 ± 337 | 647 ± 226 |
| 8 | 965 ± 166 | 367 ± 91 |
| 9 | 940 ± 220 | 361 ± 143 |
| 10 | — | — |
| 11 | — | — |
| 12 | 1539 ± 297 | 632 ± 233 |

Figure 7:
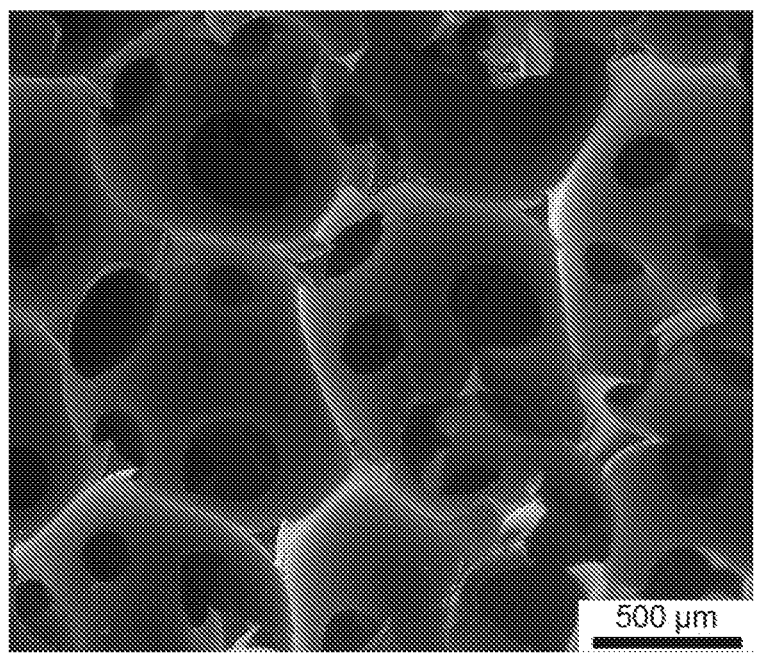
FIG. 7 shows a scanning electron microscopy (SEM) image of a biodegradable porous PEG sponge of one embodiment of the invention.

The results of the SEM evaluation showed that void volume, solvent content and pressure release were found to have an influence on pore attributes. In general, it was observed that the acid chloride/alcohol reaction with HCl gas formation leads to large rounded pores that are connected internally via smaller rounded channels as revealed by the SEM images (FIG. 7). The larger pores are likely formed due to the HCl bubbles that nucleate and expand during the exothermic reaction. The contact between the adjacent HCl bubbles that are expanding and joining together during cross-linking leads to the interconnecting channels between the pores. These channels subsequently lead to the interconnectivity of the porous PEG sponges that can be observed from the SEM images.

HCl release during the crosslinking reaction leads to a pressure increase within the container. In the study looking at various precursor (monomer) volumes, it was observed that larger precursor volumes led to a respective subsequent reduction in void volume with an increase in HCl gas production during foaming. In addition due to increased precursor amounts, the heat generated during the exothermic reaction also increases. Ensuing pressure increase that results from the heat and gas resists the expansion of the HCl bubbles within the solution, leading to smaller pore sizes. Conversely, with lower volumes, less HCl is formed and the pressure increase is smaller. This leads to a lower resistance to bubble expansion and subsequently leads to the observed larger pore and channel formation.

The effect of the precursor (monomer) concentration at a constant void volume (85.7%) on pore size distribution was studied by the addition of a solvent to the monomer composition. Thus, Examples 8 to 11 were prepared using various amounts of dichloromethane (DCM) (5, 10, 20, and 50% v/v) as a solvent and compared to their neat counterpart, Example 6.

For Examples 8 and 9 a slight decrease in both the pore and channel sizes was observed relative to Example 6 prepared in the absence of solvent. For Examples 10 and 11, no foaming was observed and non-porous cross-linked gels were obtained. At lower precursor concentrations (higher dilution) the reaction rate is reduced as evidenced by the reduced temperature change rate. Simultaneously the HCl formation rate would also be reduced. Since HCl gas is being produced slower, the bubbles would also nucleate and expand at a slower rate; producing smaller pores compared to the Example 6. When the DCM content was increased to 20 and 50% v/v there was no sponge formation. At these low concentrations the reaction rate and subsequent HCl formation rate is further reduced. Resultantly, the heat and the gas produced dissipate more readily without foaming. At higher concentrations due to the increased reaction rate, temperature is built up more rapidly. This increase in temperature then leads to rapid bubble formation and expansion.

The effect of an open environment on pore size was also studied by conducting the reaction in a non-sealed container. The resulting sponge, Example 12, was found to have a larger open pore structures with expanded pores, and channels with less spherical morphologies. This resulted in much thinner walls that formed a branching network as opposed to the compartmentalised structure of large pores connected with smaller channels obtained when the lid was sealed (Example 6). There was a significant increase in the pore and channel sizes also. Removal of the lid allows the HCl gas to escape freely without an increase in pressure in the container. Thus, the gas bubbles can readily expand, leading to the observed larger pore sizes.

Overall, evaluation of the pores for all of the porous PEG sponges (except Examples 9 and 10) revealed large pore sizes with high interconnectivity. This is suitable for tissue engineering applications whereby large sized pores would allow tissue and vascularisation to penetrate easily into the scaffold. The large pores would provide the space required for the proliferation and development of the tissue, while the interconnecting channels provide the means for cellular migration, tissue expansion and formation of vascular systems within the scaffold. The highly interconnected nature of the porous PEG sponges would also allow for easy nutrient and fluid transport as well as clearance of cellular waste products.

Mechanical Evaluation

Therefore, the mechanical integrity of the porous PEG sponges as implantable tissue engineering scaffolds was investigated via compressive testing. The porous PEG sponges were cut into cylinders (diameter=15 mm, height=10 mm) prior to testing. The sponges were not subjected to stress preconditioning prior to compressive evaluation. Cylindrical samples were placed between the metal plates of an Instron Microtester 5848 (50 N load cell) and subjected to compression of up to 80% strain. The resulting stress versus strain profiles were used to determine the compressive moduli. The results are shown in Table 6.

TABLE 6

Compressive moduli of porous PEG sponges

| Example No | Compressive Modulus (MPa) |
|---|---|
| 4 | 0.381 ± 0.05 |
| 5 | 0.212 ± 0.03 |
| 6 | 0.055 ± 0.01 |
| 7 | 0.044 ± 0.02 |
| 8 | 0.054 ± 0.01 |
| 9 | 0.022 ± 0.01 |
| 12 | 0.011 ± 0.01 |

Figure 8:
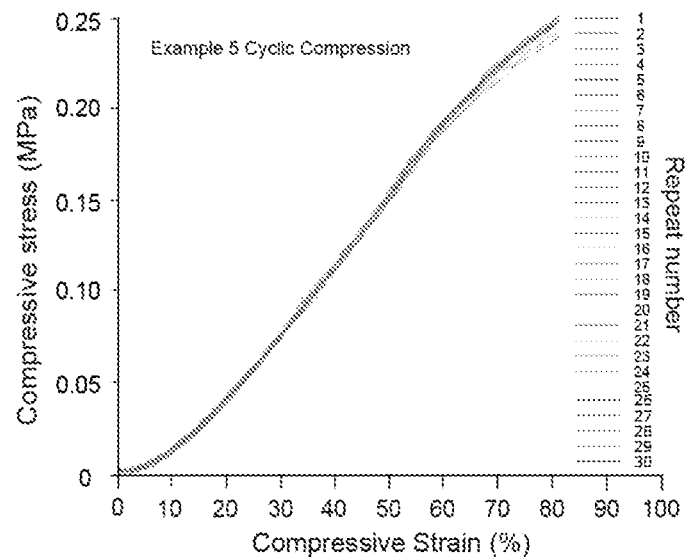
FIG. 8 shows (a) a graph illustrating a compressive stress vs. strain profile over 30 compression cycles for a biodegradable porous PEG sponge prepared with pentaerythritol ethoxylate (PE), sebacoyl chloride (SebCl) and PCL (2 wt %) of one embodiment of the invention, and (b) a graph illustrating compressive moduli for various biodegradable porous PEG sponges of embodiments of the invention.
Figure 8:
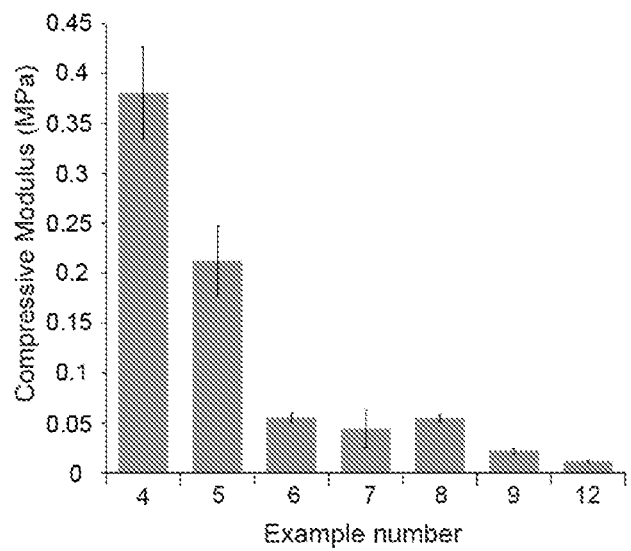

Mechanical testing of Examples 4 to 9 and 12 revealed that all of the tested porous PEG sponges displayed elastic deformation up to a compressive strain of 80% and could be repeatedly compressed before completely returning to their original dimensions. For example, repeated compression of Example 5 up to 80% revealed the same stress vs. strain profile without the presence of compressive fracture (FIG. 8(a)).

In addition to their elastic properties, the effects of fabrication conditions on the porous PEG sponges' compressive properties were investigated. Whereas Example 4 was observed to have the highest compressive modulus of ca. 380 kPa, the compressive moduli of Examples 5, 6 and 7 decreased respectively (FIG. 8(b) and Table 6). This trend can be attributed to the increasing pore sizes obtained as the precursor volume was decreased. Larger pores lead to less scaffold material per volume compared to the same volume scaffold with smaller pores. Examples 8 and 9 prepared in the presence of solvent also demonstrated slightly decreased compressive moduli compared to their neat counterpart (Example 6). The addition of solvent during the curing process reduces the rate of reaction and therefore, the cross-linking density, leading to the reduced compressive modulus. Compressive evaluation of Example 12 showed that it possessed the lowest compressive modulus (0.011 MPa) out of all the tested porous PEG sponges. This is consistent with the other porous PEG sponges and demonstrates the correlation between pore size and compressive modulus, whereby larger pores lead to lower moduli and vice versa. Examples 10 and 11 were not subjected to mechanical testing as they did not form uniform porous sponges as determined via SEM.

The moduli obtained for the porous PEG sponges are within the range for tissues, such as adipose, kidney, prostate tissue and cardiac muscle.

In Vitro Degradation Studies

To provide an indication of the hydrolytic degradation rate of the porous PEG sponges dehydrated Example 5 samples were cut into cubes (5×5×5 mm), weighed and placed into 1×PBS (20 mL, 0.01% w/v sodium azide). The vials were capped and placed into a temperature controlled orbital shaker (37° C., 100 rpm). 3 samples were removed from the orbital shaker at each time point (1, 2, 4 and 8 weeks) and soaked in deionised water for 30 min (3×20 mL). Subsequently, the sponges were dehydrated by soaking in ethanol for 1 h (2×20 mL) followed by drying in vacuo (60° C., 24 h). The sponges were then weighed and the mass values obtained were plotted against time to obtain the degradation profiles.

Figure 9:
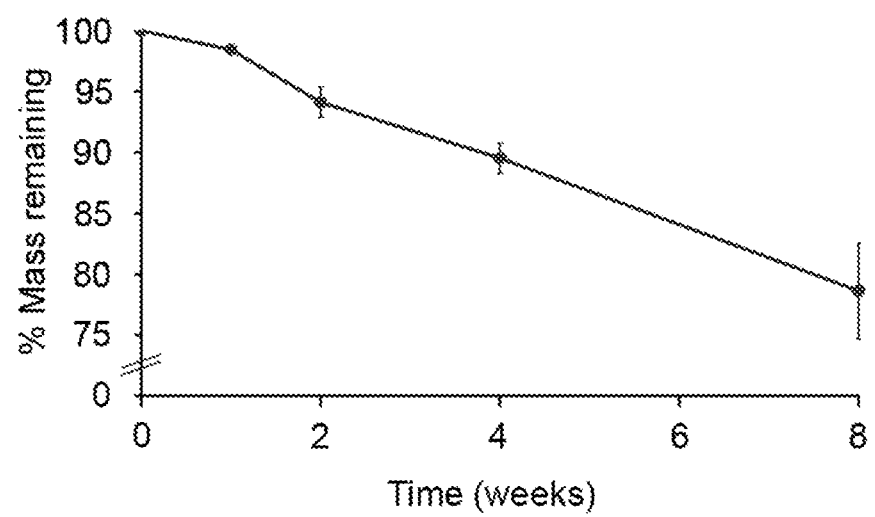
FIG. 9 is a graph showing the in vitro degradation of a biodegradable porous PEG sponge of one embodiment of the invention over 8 weeks (PBS, 37° C.).

The in vitro degradation study revealed a linear degradation profile with a mass loss of ca. 20% in 8 weeks (FIG. 9).

In Vitro Cytotoxicity Assessment of the Porous PEG Sponges and Degradation Products To assess the cytotoxicity of the porous PEG sponges, dehydrated sponges (100 mg) were placed in 80% v/v ethanol solution for 30 min. The sponges were then washed with sterile PBS for 30 min (3×20 mL), and placed in sterile DMEM (2 mL) and incubated at 37° C. for 72 h. The porous PEG sponges were then removed and the conditioned media was used in cell viability assays. To investigate the effects of degradation products on cell viability, dehydrated sponges (500 mg) were degraded in 1 M HCl (5 mL). The HCl was removed in vacuo and the residue was azeotroped with water (5×20 mL) followed by drying in vacuo (0.1 mbar, 50° C., 3 h). The degradation products (100 mg) were dissolved/resuspended in sterile DMEM (2 mL) and the solutions were sterilised under UV irradiation for 30 min and then filtered through 0.22 μm filters prior to use in the toxicity studies. NIH 3T3-L1 cells were grown to confluence in T225 flasks in DMEM at 37° C. in 5% $CO_2$ atmosphere with 95-100% humidity. The cells were trypsinised using trypsin-EDTA, counted manually using trypan blue as a live/dead stain, diluted with DMEM to reach a seeding density of $1.25×10^5$ cells/mL and plated onto 96 well plates (80 μL/well), some wells were left blank to serve as cell-blank controls. The plates were then placed in an incubator for 4 h prior to the addition of the porous PEG sponges conditioned media or degradation products. The prepared stock solutions (50 mg/mL) were twice diluted by a factor of 10 using fresh medium. 20 μL of the two dilutions thereof were added to the 96 well plates in triplicate (to obtain concentrations of 100, 1000 ppm), gently mixed by orbital movement of the plates and then the plates were returned to the incubator for a further 72 h. Following 3-days of incubation, Celltiter-AqueousOne (CAO) solution was added to the plates (20 μL/well). Plates were gently rocked to facilitate mixing and then returned to the incubator for 30 min to 4 h. At periodic intervals the UV/Vis absorbance of the plates was read at 490 nm (absorbance of product produced by metabolically active cells upon addition of the CAO reagent) and 700 nm using a Cary 50 Bio UV-Visible Spectrophotometer equipped with a micro plate reader. Usually the colour had equilibrated after approximately 2 h incubation. Absorbance values at 490 nm were corrected for background absorbance (700 nm) and absorbance of the medium alone (cell-blank controls), and then normalised to the growth control.

Figure 10:
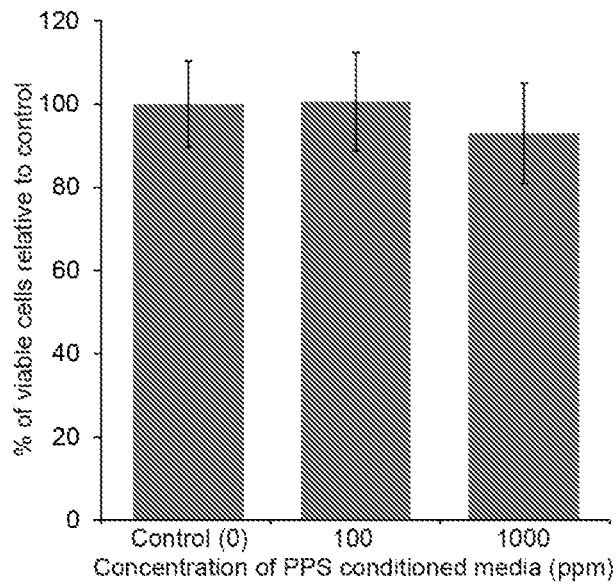
FIG. 10 shows graphs illustrating the results of a cytotoxicity evaluation of (a) a porous PEG sponge conditioned media and (b) a porous PEG sponge degradation products.
Figure 10:
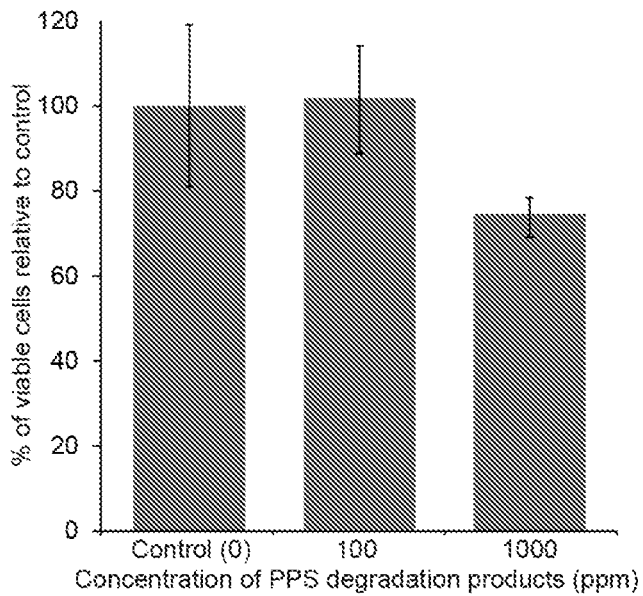

After 72 hours of incubation in the presence of various concentrations (100, 1000 ppm) of Example 5 conditioned media, minimal effect on cell viability was observed (FIG. 10(a)). In the presence of 100 ppm of the degradation products (obtained via accelerated acid catalysed hydrolysis) of Example 5 no effect on the metabolic activity of the cells was observed. However, at 1000 ppm a decrease in metabolic activity of the cells was observed and is believed to result from the high concentration of sebacic acid in the degradation products, which would decrease the pH of the media (FIG. 10(b)). It is expected that such high concentrations would not be observed in vivo as the concentrations employed for the degradation products are based upon complete degradation of the sponges in one instance.

In Vivo Evaluation of Porous PEG Sponges

Example 5 was subjected to an in vivo assay in rats using a subcutaneous pocket model. Example 5 was selected for the study as a result of its highly interconnected pore structure, compressive moduli and high stiffness, which enables it to resist compressive failure as a result of external forces when implanted.

Example 5 samples were cut into disks (10×4 mm, diameter×height) and placed into plastic vials inside doubly sealed zip-lock bags prior to gamma sterilisation. Gamma sterilisation was carried out at Steritech, Victoria, Australia (25 kGy minimum). Following sterilisation, the sponges were placed in 1× sterile PBS for 3 h prior to implantation. The sponges were implanted into 12 rats for 3 time points. All procedures were conducted according to the guidelines of the National Health and Medical Research Council (NHMRC) of Australia and were approved by the Animal Ethics Committee, St Vincent's Hospital, Melbourne. Male Sprague Dawley rats (The Animal Resources Centre (Murdoch, Western Australia), 350±50 g body weight) were kept in an approved facility and fed standard rat chow and water ad libitum. The antibiotic, enrofloxacin (Baytril 50, Bayer), was administered in the drinking water for 2 days before and 2 days after surgery to avert wound infection at a dose of 25.5 mg/kg/day. For surgery, animals were anaesthetised and maintained in an anaesthetised state using isoflurane. The skin on the dorsal surface was shaved, disinfected and four separate longitudinal incisions, approximately 1.5 cm long and 1.5 cm apart were made along the midline. Individual subcutaneous pockets for each scaffold were prepared by careful blunt dissection, on either side of the main incisions and the sponges inserted into each pocket, and anchored in place using a 3-0 prolene suture through the central hole and into the surrounding fascia. The wounds were closed using wound clips and the animals allowed to recover on a heated pad for 30 min. After periods of 2, 8 and 16 weeks following implantation, rats were anaesthetised as previously described, the original wounds reopened, the scaffolds and surrounding tissue were removed and the rats were then euthanised by intracardiac lethabarb injection. The removed sponges were cut in half, perpendicular to the circular surface and fixed with 4% paraformaldehyde solution at 4° C. for 48 h and processed through to paraffin. After processing, the explants were embedded so that complete cross-sections and the surrounding tissue could be viewed and analysed. 5 μm thick sections were cut through the mid-point of the samples and mounted on polylysine coated slides. The sections were stained with haematoxylin and eosin (H&E) and immunohistochemically using antibodies against ED1 for macrophages and giant cells.

Figure 11:
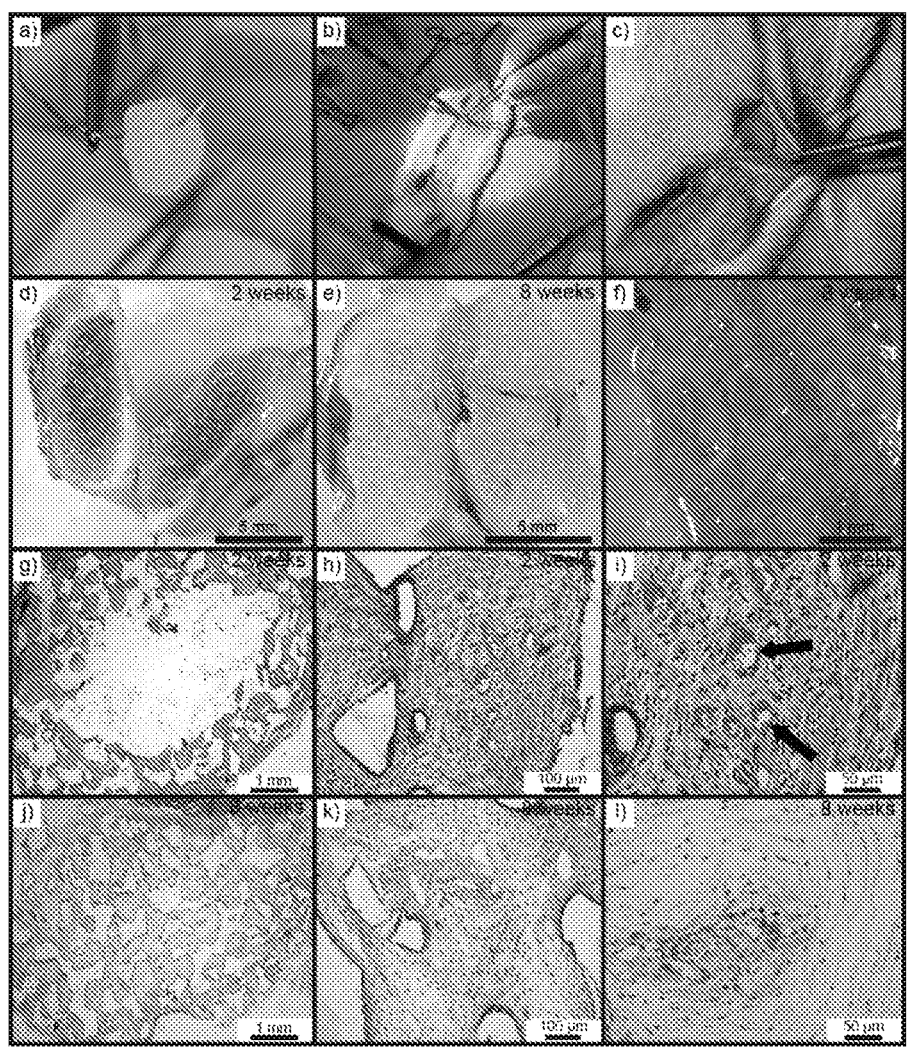
FIG. 11 shows images of (a) a biodegradable porous PEG sponge prepared with pentaerythritol ethoxylate (PE) and sebacoyl chloride (SebCl) and PCL (2 wt %) of one embodiment of the invention prior to implantation and suturing, (b) preparation of dorsal subcutaneous pockets, (c) a biodegradable porous PEG sponge being inserted into the dorsal pocket, (d) macroscopic cross-sections of a biodegradable porous PEG sponge explants at 2 weeks, (e) macroscopic cross-sections of a biodegradable porous PEG sponge explants at 8 weeks, (f) magnified cross-section of biodegradable porous PEG sponge explant at 8 weeks, H&E stained sections of biodegradable porous PEG sponge explant removed at 2 weeks at (g) 1.25×, (h) 10× and (i) 20× magnification, and H&E stained sections of biodegradable porous PEG sponge explant removed at 8 weeks at (j) 1.25×, (k) 10× and (l) 20× magnification.

Excised 2 week samples showed a thin fibrous capsule formation around the implanted porous PEG sponges with integration of the sponges into the tissue evident (FIG. 11(d)). Macroscopic observation of the sponges following bisection revealed that there was minimal change in regards to the size of the sponge after 2 weeks, with the sponges remaining intact and clearly visible, although a yellow coloration was observed, which could be indicative of degradative processes (FIG. 11(e)). Following processing into paraffin, the sponges were sectioned and subsequently stained with Haematoxylin & Eosin (H&E) to observe cellular and tissue penetration into the porous PEG sponges (FIG. 11(g)-(i)). Stained sections revealed the infiltration of dense cellular and highly vascularised tissue into the sponge from the surrounding tissue. Vascularisation can be clearly seen from the stained red blood cells indicating the location of the blood vessels (FIGS. 11(h) and (i)). Even though there was a large penetration of tissue, porous PEG sponges were not completely filled with tissue at 2 weeks, as evident from the central voids in the sections (FIG. 11(g)). Fragments of the porous PEG sponges could also be observed between the stained tissues indicating the location of the walls of the pores of the sponges (FIG. 11(h)).

Harvesting at 8 weeks also showed a thin fibrous capsule surrounding the porous PEG sponges with integration into the surrounding tissue. In contrast to the porous PEG sponges harvested at 2 weeks, macroscopic analysis of the bisected explants demonstrated the complete infiltration of uniform tissue (FIG. 11(f)). Minimal change in the size of the implants was also observed demonstrating that porous PEG sponges maintained their integrity without shrinkage. In contrast to the 2 week sections, H&E staining of the 8 week sections revealed that the porous PEG sponges were completely filled with vascularised tissue right through to the centre (FIG. 11(j)). It was also noted that the tissue present after 8 weeks was loose connective tissue, rather than the dense cellular tissue present at 2 weeks (FIG. 11(k), (l)). The vasculature observed within the sponge integrated tissue is most probably due to the induction of neovasculature from the surrounding tissue, since the porous PEG sponges were not seeded with cells or loaded with biofactors. Such vascularisation within the porous structure of a scaffold is crucial for the growth and survival of regenerating tissue.

Complete tissue infiltration demonstrates the highly interconnected nature of the pores of the porous PEG sponges. Since no cells were seeded and no biofactors were incorporated into the porous PEG sponges, the tissue developed within the porous PEG sponges pores must have infiltrated from the surrounding tissue, hence the penetration of cells and vascular tissue by 2 weeks and complete infiltration by 8 weeks, demonstrate permeance of the porous PEG sponges to cellular tissue and vascularisation. Thus, the porous PEG sponges are able to provide a 3D environment that is suitable for cellular and vascular integration, and ensure the survival of the infiltrated tissue.

Figure 12:
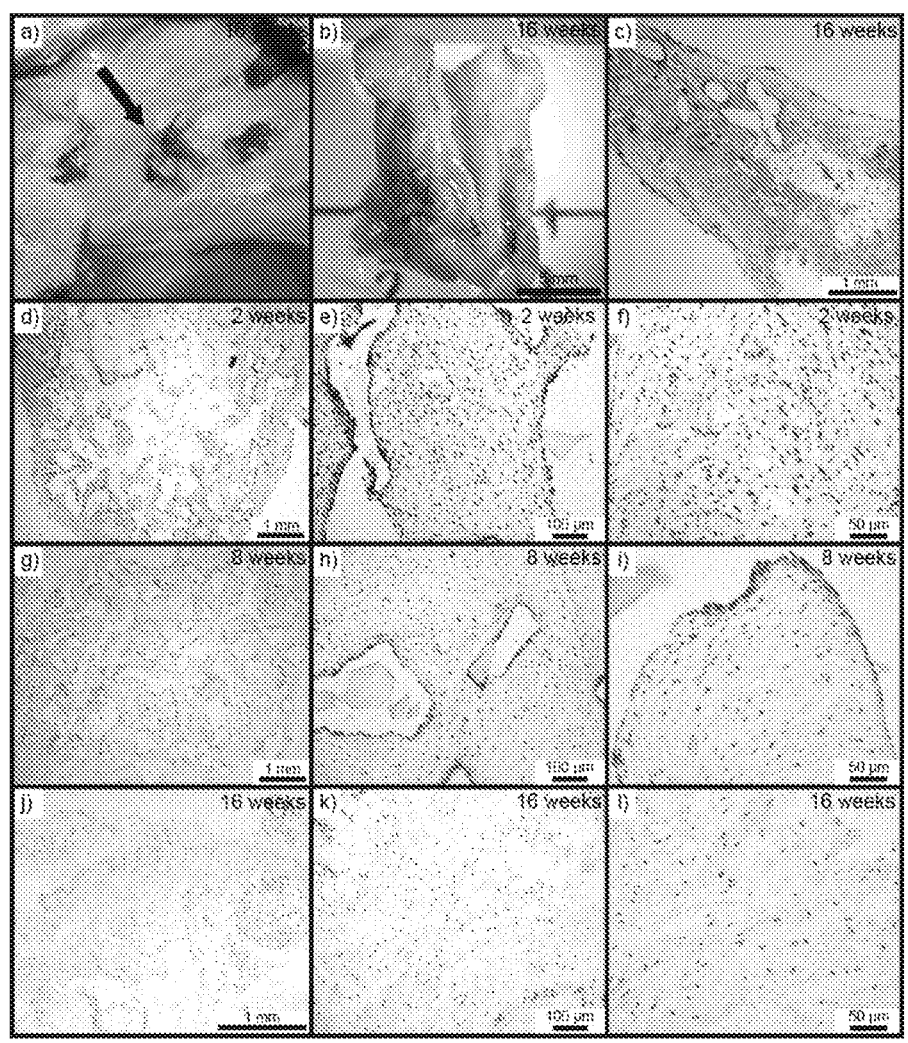
FIG. 12 shows (a) location of implanted a biodegradable porous PEG sponge prepared with pentaerythritol ethoxylate (PE) and sebacoyl chloride (SebCl) and PCL (2 wt %) of one embodiment of the invention after 16 weeks, (b) macroscopic cross-section of the biodegradable porous PEG sponge removed at 16 weeks, (c) H&E stained section of tissue where the biodegradable porous PEG sponge was implanted, ED1 stained sections of the biodegradable porous PEG sponge removed at 2 weeks at (d) 1.25×, e) 10× and f) 20× magnification, ED1 stained sections of the biodegradable porous PEG sponge removed at 8 weeks at (g) 1.25×, (h) 10× and (i) 20× magnification, and ED1 stained section of tissue in the implantation site at 16 weeks at (j) 1.25×, (k) 10× and (l) 20× magnification.

At 16 weeks, harvesting of the implants revealed macroscopically that it was very difficult to locate the implants. There was no evidence of implant protrusions in contrast to 2 and 8 weeks. Instead, the location of the porous PEG sponges was discerned by the presence of the sutures originally used to secure them into place. There was no macroscopic evidence of any adverse effects adjacent to the suture. Presence of a small amount of solid tissue was observed attached to the suture (FIG. 12(a)). Tissue attached and surrounding the suture was dissected and processed for histology.

H&E staining was carried out to discern the tissue morphology and see if the presence of porous PEG sponges could be observed. Analysis of the H&E stained sections revealed that by 16 weeks there was no evidence of porous PEG sponges remaining in any of the implant sites (FIG. 12(c)). Surrounding tissue was unremarkable dense cellular and vascular tissue. This indicates that in 16 weeks the porous PEG sponges are completely degraded, demonstrating their in vivo biodegradability.

Innate immune response towards an implant can be recognised via observing the presence of macrophages and foreign body giant cells (FBGC). As a means of determining macrophage and FBGC infiltration ED1 immunostaining was carried out on all the sections from the three time points (FIG. 12(d)-(l)). Analysis of the 2 week samples revealed the presence of macrophages as predicted. Macrophages observed by the ED1 staining at 2 weeks were mainly present at the scaffold/tissue interface, whereas the central tissue was dominated by non-inflammatory cells (FIG. 12(d)-(f)). Analysis of the ED1 stained 8 weeks sections revealed that the macrophage response had reduced significantly and were much smaller in size (FIG. 12(g)-(i)). The tissue stained was dominated by non-inflammatory cells even at the scaffold/tissue interface, demonstrating the reduced response towards the sponge material. By 16 weeks the porous PEG sponges had completely degraded, thus ED1 staining would reveal whether there was a major response to the porous PEG sponges and ultimately their degradation products. ED1 stained 16 weeks sections showed almost no presence of macrophages (FIG. 12(j)-(l)). This demonstrates that overall, the porous PEG sponges and their degradation products initially result in a minor inflammatory response, and this response diminishes over time.

The in vivo study revealed that the tissue responses and interaction towards the porous PEG sponges were very positive and the outcomes are highly promising. By permitting the infiltration, vascularisation and survival of tissue within their porous 3D structure, the porous PEG sponges are excellent candidates for tissue regeneration. Together with their minimal immunogenicity, tissue infiltration and complete biodegradation without toxicity in 16 weeks, the porous PEG sponges possess highly desirable properties as scaffolds for tissue engineering.

Porous Biodegradable Polyethylene Glycol) (PEG) Sponge with Controlled Physical Properties Herein we describe the fabrication and characterisation of porous PEG hydrogels having controllable pores size produced via a salt leaching technique. In addition, three cross-linkers; sebacoyl chloride, succinyl chloride, and trimesoyl chloride were utilised to control mechanical and degradation characteristics of the resultant network polymer.

Materials

Pentaerythritol ethoxylate (Mn ~797 Da), poly(ethylene glycol) ($M_n$~600 Da) sebacoyl chloride (≥95%), succinyl chloride (95%), 1,3,5-benzenetricarbonyl trichloride (trimesoyl chloride) (98%), ε-caprolactone (97%), 2,2'-dithiodiethanol (90%), stannous octanoate (~95%), toluene (anhydrous, 99.8%) and phosphate buffered saline (PBS) tablets were obtained from Sigma-Aldrich and were used as received. Dulbecco's Modified Eagle Medium (DMEM), Fetal Bovine Serum (FBS), L-glutamine, trypsin-EDTA (0.05%), trypan blue (0.4%) and penicillin-streptomycin were obtained from GIBCO. DMEM was supplemented with 10% v/v FBS, 1% v/v L-glutamine and 1% v/v penicillin-streptomycin prior to use for the cell viability assays. NUNC T225, canted neck flasks were obtained from Thermo Fisher Scientific. Dichloromethane (≥99.5%), tetrahydrofuran (THF) (Honeywell, 99.99%), ethanol (undenatured 100%), sodium carbonate (≥99.2%, anhydrous) were obtained from Chem-Supply and were used as received. CelltiterAqueousOne solution for cell viability assays was obtained from Promega and used as received. Matrix assisted laser desorption/ionisation time-of-flight mass spectroscopy (MALDI ToF MS) matrix trans-2-[3-(4-tert-butylphenyl)-2-methyl-2-propenylidene]malononitrile (DCTB) 99.0) and cationisation agent (NaTFA (99.999%)) were purchased from Aldrich and used as received.

Fused Salt Template Preparation

Crystalline sodium chloride (NaCl) was initially ground in a mortar and pestle and then sieved (Endecotts Ltd. (London, England) set of standard laboratory test sieves) to obtain 300-600 μm sized salt particles. 4 g of salt particles were weighed and placed inside polyethylene vials (28 mL) and were compressed gently with a cylindrical metal compressor. The vials were then transferred into a humidifier and were maintained in the humidifier at room temperature (80% humidity) for 24 h to produce the fused salt templates. The fused templates were then dried under house vacuum for 18 h (100° C., 20 mbar), capped and placed in a desiccator until further use.

Synthesis of α,ω-Dihydroxyl-PCL (Mechanical Property Modifier)

α,ω-Dihydroxyl PCL was prepared via ring-opening polymerisation (ROP); ε-caprolactone (20.0 g, 175 mmol), 2,2'-dithiodiethanol (1.08 g, 7.00 mmol) and stannous octoate (0.95 g, 2.34 mmol) were dissolved in anhydrous toluene (45 mL) and heated at 110° C. under argon for 24 h. The mixture was cooled to room temperature, diluted with THF (50 mL) and precipitated into cold methanol (−18° C., 1 L). The precipitate was collected by filtration and dried in vacuo (0.1 mbar) to afford α,ω-dihydroxyl PCL as a white powder, 18.8 g (94%); $M_n$ (NMR)=3.2 kDa, $M_n$ (MALDI ToF)=3.3 kDa (PDI=1.07).

Preparation of Salt-Templated Biodegradable Porous Poly (Ethylene Glycol) (PEG) Sponges Poly(ethylene glycol) (PEG600) (0.75 g, 1.255 mmol), pentaerythritol ethoxylate (PE) (0.50 g, 0.63 mmol), and 0 mg, 33 mg or 82 mg of dihydroxy-PCL (corresponding to 0, 2, or 5 wt % PCL, respectively) were dissolved in dichloromethane (DCM, 10% v/v) (Table 7). Subsequently sebacoyl chloride (SebCl) (0.60 g, 2.51 mmol), succinyl chloride (SucCl) (0.39 g, 2.51 mmol), or trimesoyl chloride (TmsCl) (1.27 g, 4.77 mmol) was added. The monomer composition was vortexed for 10 s and immediately, 1.2 mL of this solution was pipetted into the vial containing the fused salt template and centrifuged for 30 s. The vial was then placed into the oven at 60° C. for 1 h and vacuumed for 24 h (20 mbar, 60° C.) in a vacuum oven. The cross-linked gel was removed from the vial and placed in deionised water with gentle stirring (100 mL). The water was changed every 30 min for 2 h and then every hour for 3 h before a final exchange for 24 h. The swollen polymers were then placed in a sodium carbonate solution for 2 h with gentle stirring and washed with deionised water for 30 mins (3×100 mL) to neutralise any HCl. The produced porous PEG sponges were then stored in PBS prior to characterisations.

TABLE 7

| Example No | PE (g) | PEG$_{600}$ (g) | Dihydroxy PCL (mg) | 10% (v/v) DCM (μl) | SucCl (g) | SebCl (g) | TmsCl (g) |
|---|---|---|---|---|---|---|---|
| 13 | 0.50 | 0.75 | 0 | 151 | 0.39 | — | — |
| 14 | 0.50 | 0.75 | 33 | 151 | 0.39 | — | — |
| 15 | 0.50 | 0.75 | 82 | 151 | 0.39 | — | — |
| 16 | 0.50 | 0.75 | 0 | 180 | — | 0.60 | — |
| 17 | 0.50 | 0.75 | 37 | 180 | — | 0.60 | — |
| 18 | 0.50 | 0.75 | 93 | 180 | — | 0.60 | — |
| 19 | 0.50 | 0.75 | 0 | 170 | — | — | 0.67 |
| 20 | 0.50 | 0.75 | 38 | 170 | — | — | 0.67 |
| 21 | 0.50 | 0.75 | 96 | 170 | — | — | 0.67 |

To produce the interconnected porous structure for tissue penetration and vascularisation, the sacrificial fused sodium chloride templates were used. Following cross-linking, the porous PEG sponges were vacuumed at 60° C. for 24 h and placed in deionised water to swell the porous PEG sponges and remove the salt template.

Porous PEG sponges produced with succinyl chloride (SucCl), sebacoyl chloride (SebCl) and trimesoyl chloride (TmsCl) were termed Suc-SPH, Seb-SPH and Tms-SPH, respectively.

Swelling Studies

Swelling studies were conducted to determine the water uptake of the porous PEG sponges. Dehydrated porous PEG sponges (1×1×1 cm³) were weighed and then immersed in Milli-Q water for 48 h. The percentage equilibrium solvent ratio (% ESR) of the hydrogels was calculated using the equation % ESR=$((W_s-W_d)/W_d)\times 100\%$, where $W_s$ and $W_d$ refer to the swollen and dried weights, respectively. The analysis was conducted in triplicate for each type of polymer and the results averaged. The results are shown in Table 8.

TABLE 8

| Example No | PCL Content (wt %) | % ESR | Average pore size (μm) |
|---|---|---|---|
| 13 | 0 | 1209 ± 65 | — |
| 14 | 2 | 1184 ± 56 | 456 ± 114 |
| 15 | 5 | 1139 ± 52 | — |
| 16 | 0 | 327 ± 4.5 | — |
| 17 | 2 | 310 ± 2.1 | 467 ± 118 |
| 18 | 5 | 301 ± 2.3 | — |
| 19 | 0 | 370 ± 6.3 | — |
| 20 | 2 | 340 ± 0.9 | 477 ± 102 |
| 21 | 5 | 321 ± 5.5 | — |

The difference in polymers prepared with different cross-linking monomers SebCl, SucCl, and TmsCl were evident in the measured Equilibrium Swelling Ratios (% ESR). Examples 13 to 16, prepared with SucCl, all displayed a much higher ESR compared to its SebCl and TmsCl counterparts. This can be attested to the hydrophobicity of the SebCl and TmsCl. The longer alkyl backbone of SebCl and the benzene ring of TmsCl create a more hydrophobic environment compared to the SucCl within the crosslinked polymer network hence reducing the water absorbing capabilities of the porous PEG sponges. The SucCl has a shorter alkyl backbone hence the porous PEG sponges produced are less hydrophobic and absorb more water.

The PCL content of the porous PEG sponges were also varied from 0 wt %, 2 wt % and 5 wt % and it was observed that there was a reduction in the % ESR with increasing PCL content for the hydrogels prepared from all cross-linkers. This is consistent with the effects of hydrophobicity observed with SebCl and TmsCl. PCL is a hydrophobic polymer, hence the increased amount of PCL also leads to a lower % ESR.

Pore Size Analysis

Porous PEG sponges with 2 wt % PCL were swollen in 1×PBS, then cut in half and mounted on a carbon tab. The exposed internal surfaces were analysed using a FEI Quanta FEG 200 E-SEM under low vacuum conditions to observe the porous structure of the hydrogels. ImageJ (National Health Institute, USA) software was utilised to determine the average pore sizes.

Figure 13:
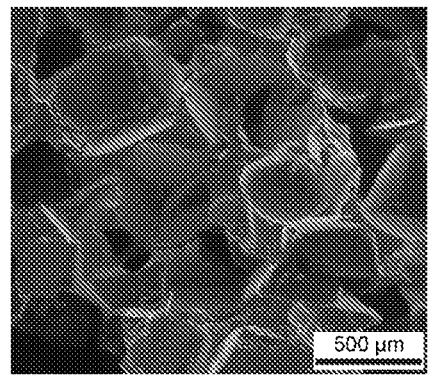
FIG. 13 illustrates Enviro-SEM images of biodegradable porous PEG sponges of embodiments of the invention formed with salt templates and with (a) succinyl chloride crosslinking monomer and 2 wt % PCL (b) sebacoyl chloride crosslinking monomer and 2 wt % PCL, and (c) trimesoyl chloride crosslinking monomer and 2 wt % PCL.
Figure 13:
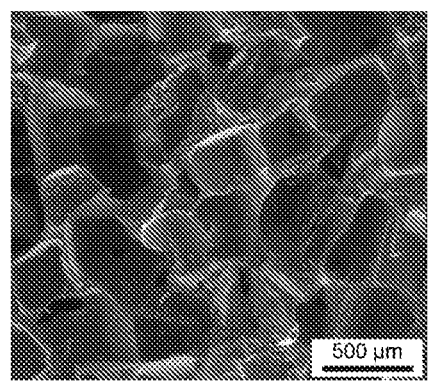
Figure 13:
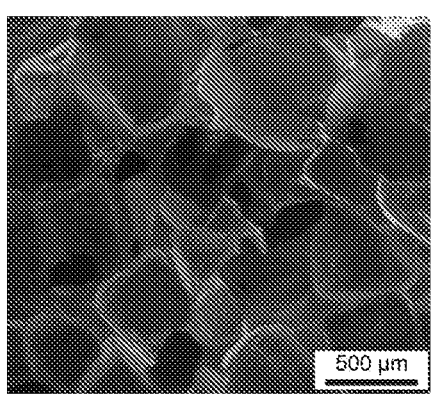

SEM revealed that the pore sizes observed within the porous PEG sponges prepared with the various crosslinking monomers correlated well with the prepared fused salt templates and were observed to be interconnected (FIG. 13). The average pore sizes obtained are shown in Table 8. The prepared salt particles ranged from 300-600 μm in size, thus the average sizes obtained for the porous PEG sponges correlate very well with the prepared salt particles.

Also a significant difference in pore size between porous PEG sponges prepared with different cross-linkers was not observed, even though there was a difference in the swelling between the polymers. This demonstrates the pore sizes remain unaffected regardless of the swelling properties. These large sized pores for all the porous PEG sponges would allow tissue and vascularisation to penetrate easily into the scaffold. The large interconnected pores would provide the space required for the proliferation and development of the tissue and formation of vascular systems within the scaffold. The interconnected nature of the porous PEG sponges would also allow for nutrient and fluid transport as well as clearance of cellular waste products.

In regards to the salt-templating technique, it is possible to control the pore size of the hydrogels since the porogen (salt) particle size can be directly tailored to a specific range. This can be advantageous for specific tissue types where certain pore sizes were found to be better suited for specific tissue and cell types.

Mechanical Evaluation of Porous PEG Sponges

Swollen porous PEG sponges were cut into cubes (1×1×1 cm³) prior to compressive testing. The porous PEG sponges were not subjected to stress preconditioning prior to compressive evaluation. Cubic samples were placed between the metal plates of the Instron Microtester 5848 (with 50 N load cell) and were subjected to compression up to 80% strain. The resulting stress versus strain profiles were used in determination of the compressive moduli of the porous PEG sponges. Some porous PEG sponges were also subjected to cyclic compression up to 80% strain to determine their elastic properties. The results are shown in Table 9.

TABLE 9

| Example No | PCL Content (wt %) | Ultimate stress (MPa) | Ultimate elongation (%) | Compressive Modulus (kPa) |
|---|---|---|---|---|
| 13 | 0 | 33 ± 3.4 | 46 ± 2.0 | 81.0 ± 11 |
| 14 | 2 | 51 ± 5.3 | 58 ± 2.1 | 89.0 ± 0.1 |
| 15 | 5 | 83 ± 4.2 | 75 ± 4.1 | 81.0 ± 10 |
| 16 | 0 | — | — | 183 ± 28 |
| 17 | 2 | — | — | 250 ± 20 |
| 18 | 5 | — | — | 330 ± 5.7 |
| 19 | 0 | 124 ± 18 | 60 ± 9.2 | 192 ± 6.0 |
| 20 | 2 | — | — | 148 ± 3.0 |
| 21 | 5 | — | — | 193 ± 6.0 |

Figure 14:
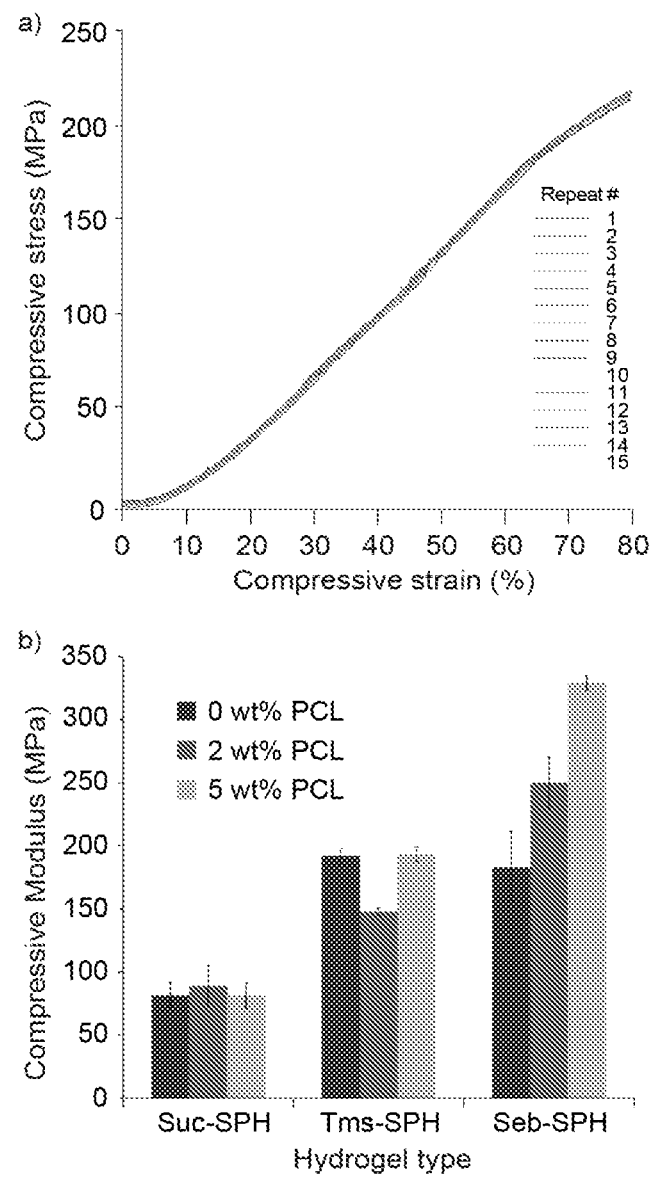
FIG. 14 shows (a) a graph illustrating the compressive moduli of biodegradable porous PEG sponges prepared with salt templates and different wt % PCL in accordance with embodiments of the invention, and (b) a graph illustrating the compressive stress vs. strain profile for a biodegradable porous PEG sponge of one embodiment prepared with salt templates, sebacoyl chloride crosslinking monomer and 2 wt % PCL during 15 compression cycles.

For the different cross-linkers used, different compressive behaviours were observed. Elastic 'J' shaped compressive stress vs. strain profiles were obtained for all PCl containing polymer networks prepared with SebCl and TmsCl. The SebCl polymers, and PCL containing TmsCl polymers maintained their elastic structure. Sebcl polymers remained elastic without fracture even after repeated compressions up to 80% (FIG. 14(a)). The compressive moduli of the SebCl polymers increased from ca. 180 kPa, to ca. 250 and 330 kPa to with increasing dihydroxy PCL content from 0 wt % to 2 and 5 wt % respectively.

Porous PEG sponges prepared with SucCl on the other hand displayed a 'Newtonian', linear stress vs. strain behaviour and fractured between ca. 45 to 70% compressive strains with increasing PCL content (Table 9). These polymers displayed improved fracture stresses and strains as the PCL content was increased. The compressive moduli though were not affected significantly (FIG. 14(b)).

Porous PEG sponges prepared with TmsCl did not initially possess the highly elastic nature of the PEG sponges prepared with SebCl until the incorporation of PCL. Following PCL incorporation, the TmsCl sponges also maintained an elastic structure that demonstrated resistance up to 80% compression (FIG. 14(b), Table 9).

In Vitro Degradation Study of Porous PEG Sponges

Porous PEG sponges were cut into cubes (5×5×5 mm), dehydrated in ethanol and dried overnight in a vacuum oven (60° C.). Dried samples were weighed and placed into 1×PBS (20 mL, 0.01% w/v sodium azide). The vials were sealed and placed into a temperature controlled orbital shaker (37° C., 100 rpm). 3 samples were removed from the orbital shaker at each time point (1, 2, 4 and 8 weeks) and washed in deionised water for 30 min (3×20 mL). Subsequently, the polymers were dehydrated by soaking in ethanol for 1 h (2×20 mL) followed by drying in vacuo (60° C., 24 h). The dried samples were then weighed and the mass values obtained were plotted against time to obtain the degradation profiles.

Figure 15:
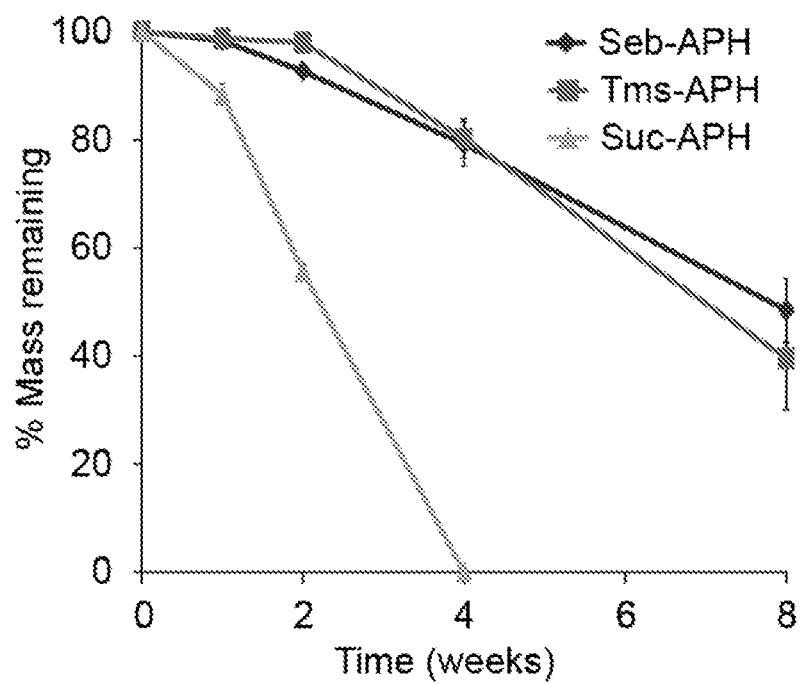
FIG. 15 illustrates a graph showing in vitro degradation of biodegradable porous PEG sponges prepared with different crosslinking monomers in accordance with embodiments of the invention prepared with salt templates over 8 weeks (PBS, 37° C.).

The degradation study revealed that porous PEG sponges prepared with TmsCl had a mass loss of ca. 40% in 8 weeks, while those prepared with SebCl had a mass loss ca. 35% over 8 weeks. Porous PEG sponges prepared with SucCl had completely degraded by 4 weeks (FIG. 15).

In Vitro Cytotoxicity Evaluation of Porous PEG Sponges

For the cytotoxicity evaluation of the porous PEG sponges, two types of samples were prepared. To assess the cytotoxicity of the porous hydrogels, dried porous PEG sponges were weighed and 100 mg was placed in 80% v/v ethanol solution for 30 min. The porous PEG sponges were then washed and rehydrated with sterile PBS (3×20 min) and placed in 2 mL of sterile DMEM and subsequently incubated at 37° C. for 72 h. The porous PEG sponges were then removed and the conditioned media was used in the cell viability assay. To investigate the effects of hydrogel degradation products on cell viability, dried hydrogel (500 mg) was degraded in 1M HCl solution (5 mL). HCl was removed azeotropically in vacuo with water (5×20 mL) and finally dried under high vacuum. 100 mg of degradation products were weighed and dissolved/resuspended in 2 mL of sterile DMEM. The solutions were then sterilised under UV for 30 min and filtered through 0.22 μm filters prior to use in the toxicity studies. NIH 3T3-L1 cells were grown to confluence in T225 flasks in DMEM at 37° C. in 5% $CO_2$ atmosphere with 95-100% humidity. Cells were trypsinised using 0.05% Trypsin-EDTA, counted manually using trypan blue as live/dead stain, diluted with fresh medium to reach a seeding density of $1.25×10^5$ cells/mL and plated onto 96 well plates (80 μL/well), some wells were left blank to serve as cell-blank controls. The plates were returned to the incubator for 4 h prior to addition of the porous PEG sponges conditioned media and degradation products. The prepared stock solutions (50 mg/mL) were twice diluted by a factor of 10 using fresh complete medium. 20 μL of the dilutions thereof were added to the 96 well plates in triplicate (to obtain concentrations of 100 and 1000 ppm), gently mixed by orbital movement of the plates and then the plates were returned to the incubator for a further 72 h incubation. Following incubation, CelltiterAqueousOne Solution was added to the plates (20 μL/well). Plates were gently rocked to facilitate mixing and then returned to the incubator for 30 min-4 h. In periodic intervals the UV-Vis absorbance of the plates was observed at 490 nm and 700 nm using a Cary 50 Bio UV-Visible Spectrophotometer equipped with a micro plate reader. The colour had equilibrated after approximately 2 h incubation. Absorbance values at 490 nm were corrected for background absorbance (700 nm) and absorbance of the medium alone (cell-blank controls), and then normalised to the growth control.

Figure 16:
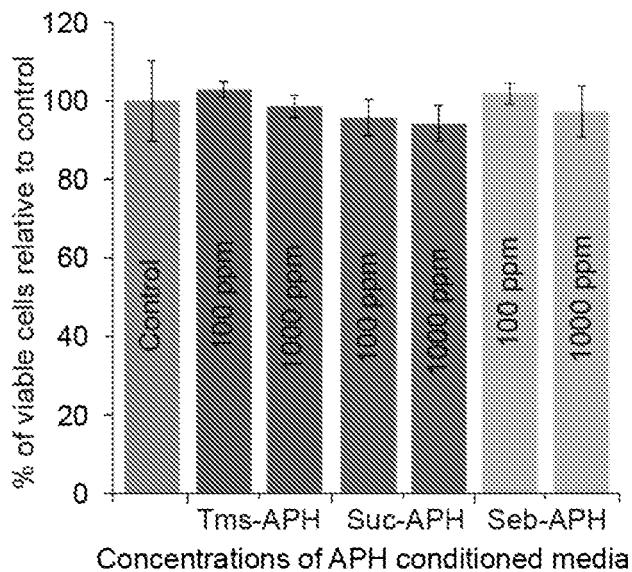
FIG. 16 shows graphs illustrating the results of a cytotoxicity evaluation of (a) conditioned media and (b) degradation products obtained from porous PEG sponges of embodiments of the invention prepared with different crosslinking monomers.
Figure 16:
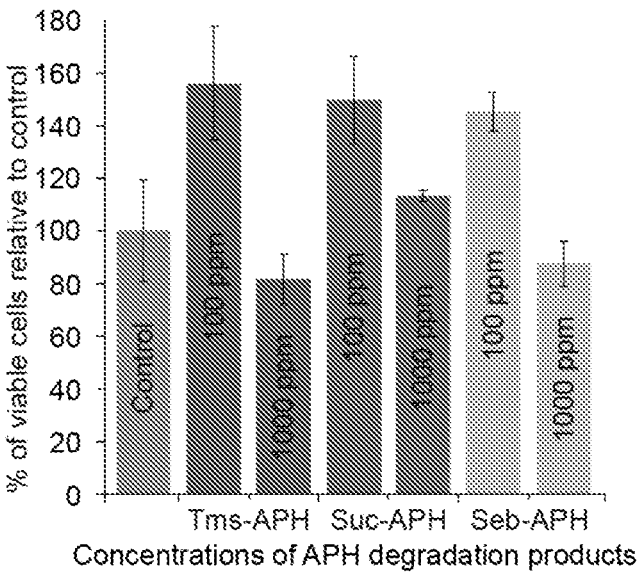

After 72 hours of incubation in the presence of various concentrations (100 and 1000 ppm) of porous PEG sponge conditioned media, minimal effect on cell viability was observed (FIG. 16(a)) for all of the cross-linkers. In the presence of the degradation products obtained via rapid acid mediated degradation, no significant effect was observed at 100 ppm on the metabolic activity of cells (FIG. 16(b)). On the other hand a small reduction in metabolic activity was observed at 1000 ppm, but relative to the control this difference is minimal.

In Vivo Evaluation of Porous PEG Sponges

Swollen porous PEG sponges prepared with sebacoyl chloride (2 wt % PCL) (Example 17) were cut into disks 10×4 mm (diameter×height) dried in vacuo (20 mbar, 60° C.) and were placed into plastic vials and doubly sealed in zip-lock bags prior to gamma irradiation for sterilisation. Gamma sterilisation was carried out at Steritech, Victoria, Australia (25 kGy minimum). Following sterilisation, the hydrogels were placed in 1× sterile PBS, 3 hours prior to implantation. The porous PEG sponges were implanted into 12 rats for 3 time points. All procedures were conducted according to the guidelines of the National Health and Medical Research Council (NHMRC) of Australia and were approved by the Animal Ethics Committee, St Vincent's Hospital, Melbourne. Male Sprague Dawley rats (The Animal Resources Centre (Murdoch, Western Australia), (350±50 g body weight) were kept in an approved facility and fed standard rat chow and water ad libitum. The antibiotic, enrofloxacin (Baytril 50, Bayer), was administered in the drinking water for 2 days before and 2 days after surgery to avert wound infection at a dose of 25.5 mg/kg/day. For surgery, animals were anaesthetised and maintained in an anaesthetised state via isoflurane. The skin on the dorsal surface was shaved, disinfected and four separate longitudinal incisions, approximately 1.5 cm long and 1.5 cm apart were made along the midline. Individual subcutaneous pockets for each scaffold were prepared by careful blunt dissection, on either side of the main incisions and the hydrogels inserted into each pocket, and anchored in place using a 3-0 prolene suture through the central hole and into the surrounding fascia. The wounds were closed using wound clips and the animals allowed to recover on a heated pad for 30 min. After periods of 2, 8 and 16 weeks following implantation, rats were anaesthetised as previously described, the original wounds reopened, the hydrogel scaffolds and surrounding tissue was removed and the rats were then euthanised by intracardiac lethobarb injection. The removed porous PEG sponges were cut in half, perpendicular to the circular surface and fixed with 4% paraformaldehyde solution at 4° C. for 48 h and processed through to paraffin. After processing, the explants were embedded so that complete cross-sections and its surrounding tissue could be viewed and analysed. 5 μm thick sections were cut through the mid-point of the samples and mounted on poly-lysine coated slides. The sections were stained with haematoxylin and eosin (H&E), and immunohistochemically using antibodies against ED1 for macrophages and giant cells.

Figure 17:
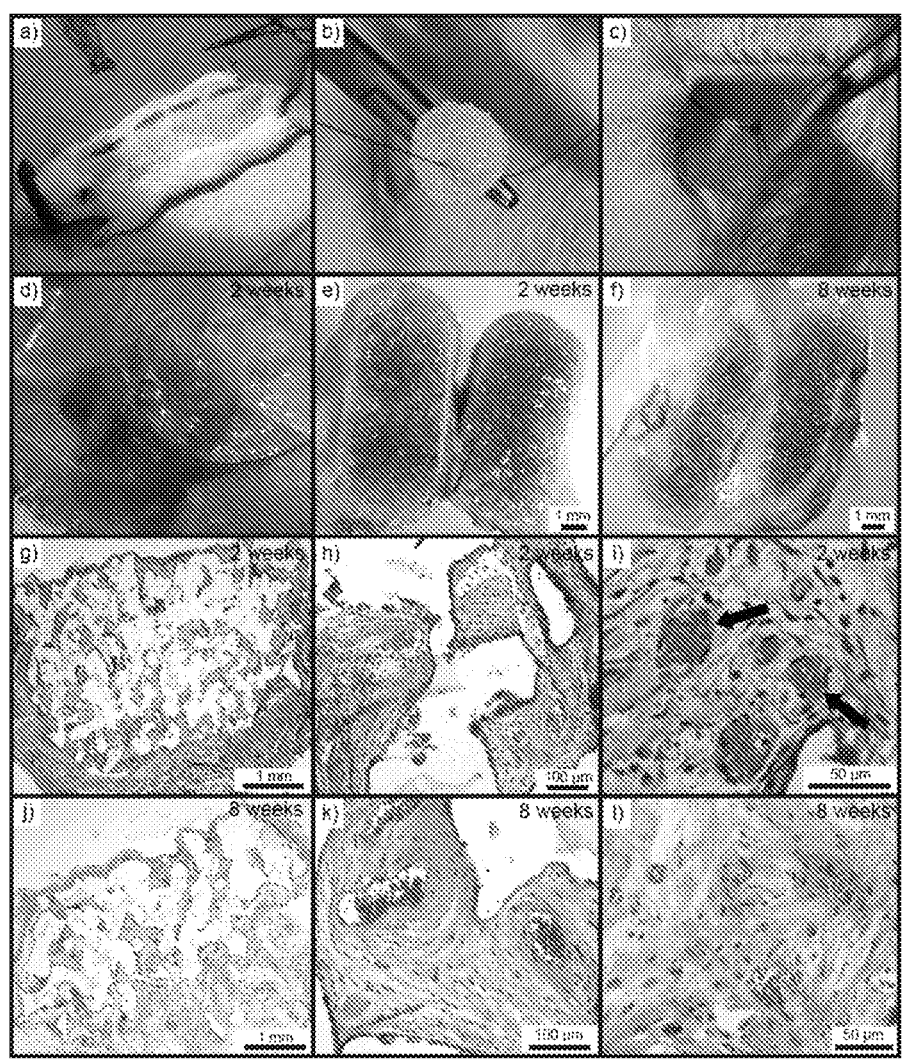
FIG. 17 shows (a) prepared subcutaneous pockets for implantation of a biodegradable porous PEG sponge prepared with salt templates and sebacoyl chloride crosslinking monomer in accordance with embodiments of the invention, (b) the biodegradable porous PEG sponge prior to implantation and suturing, (c) the biodegradable porous PEG sponges inserted and sutured into the dorsal pocket. (d) the biodegradable porous PEG sponge prior to excision from implantation site after 2 weeks, (e) macroscopic cross-sections of the biodegradable porous PEG sponge explants at 2 weeks, (f) the biodegradable porous PEG sponge explants at 8 weeks, H&E stained sections of the biodegradable porous PEG sponge removed at 2 weeks at (g) 1.25×, (h) 10× and (i) 20× magnification, H&E stained sections of the biodegradable porous PEG sponge removed at 8 weeks at (j) 1.25×, (k) 10× and (l) 20× magnification.

After 2 week implantation the porous PEG sponges were well integrated into the tissue with only a thin capsule formation (FIG. 17d). Minimal change in regards to the size of the hydrogel was observed after 2 weeks; with the polymer sponges remaining intact and clearly visible (FIG. 17e). Following processing into paraffin, the polymer sponges were sectioned and subsequently stained with H&E to observe cellular and tissue penetration into the polymer sponges (FIG. 17g-i). H&E stained sections showed the infiltration of dense cellular and highly vascularised tissue into the hydrogel from the surrounding tissue. Blood vessels can be clearly seen from the stained red blood cells indicating the location of vasculature (FIG. 17h-i). It was possible to see that the vascularised tissue was able to penetrate to the centre of the polymer sponges from the surrounding tissue as evidence by the H&E stained sections. The large gaps observed in the stained sections are likely due to the shrinkage of the porous PEG sponges pore walls and the penetrated tissue due to dehydration caused by processing into paraffin.

8 weeks harvest also showed a thin fibrous capsule surrounding the porous PEG sponges with integration into the surrounding tissue. Bisection of the harvested tissue showed a decrease in thickness of the size of the explant and a yellowing of the polymer sponge material was observed. Infiltration of tissue to the centre of the scaffolds was confirmed via H&E staining, but a significant difference in the amount of penetrated tissue was not observed (FIG. 17j). Although, it was noted that the tissue present after 8 weeks was loose connective tissue, rather than the dense cellular tissue present at 2 weeks (FIG. 17k, l). The vascularisation of the porous PEG sponges is most probably due to neovascularisation from the surrounding tissue, as cell or biofactor loading was not carried out.

Penetration of vascularised tissue to the centre of the polymer sponges demonstrates the interconnected nature of the pores of the porous PEG sponges. The penetration of cells and vascular tissue by 2 weeks, demonstrate that porous PEG sponges are permeable to cellular tissue and vascularisation. Thus, the porous PEG sponges possess a 3D environment that is appropriate for cellular and vascular integration, and ensure the survival of the infiltrated tissue.

Figure 18:
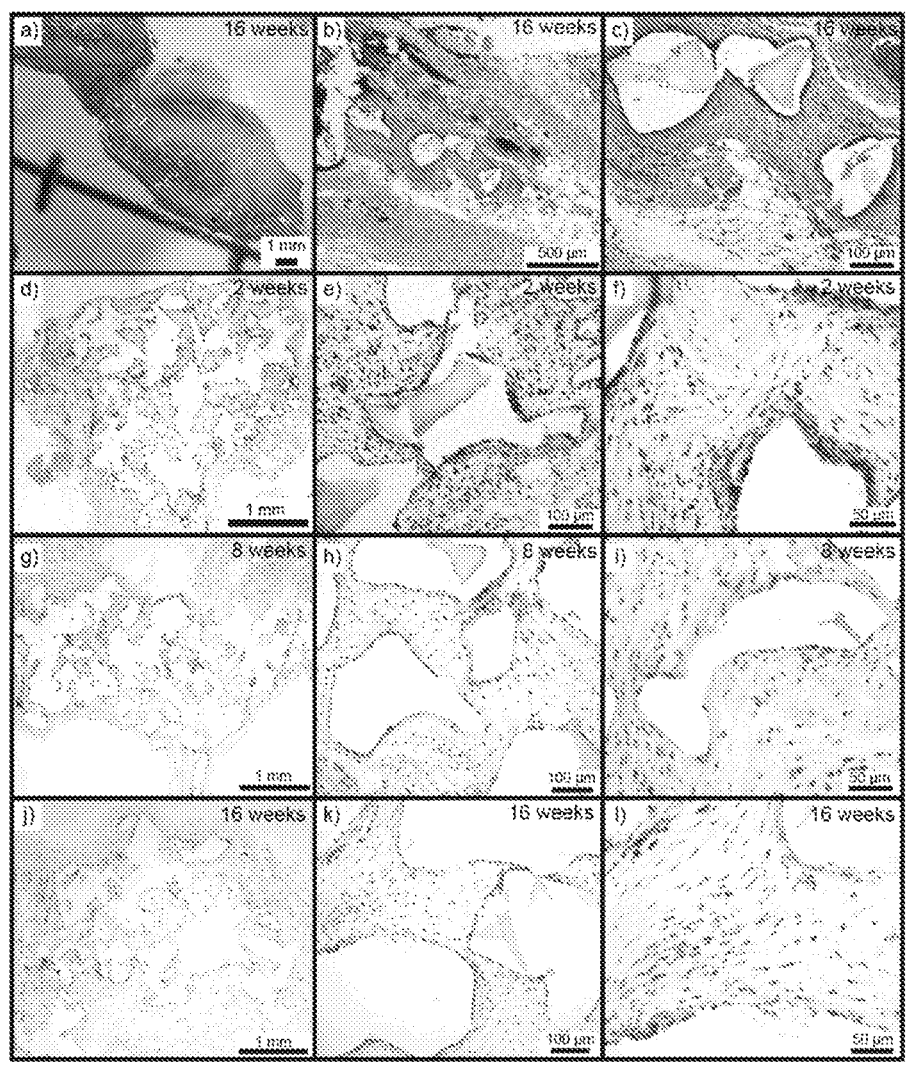
FIG. 18 shows (a) macroscopic cross-section of a biodegradable porous PEG sponges prepared with salt templates and sebacoyl chloride crosslinking monomer in accordance with embodiments of the invention removed at 16 weeks, H&E stained section of tissue where the biodegradable porous PEG sponge was implanted at (b) 1.25× magnification (c) 10× magnification, ED1 stained sections of the biodegradable porous PEG sponge removed at 2 weeks at (d) 1.25×, e) 10× and (f) 20× magnification, ED1 stained sections of the biodegradable porous PEG sponge removed at 8 weeks at (g) 1.25×, (h) 10× and (i) 20× magnification, and ED1 stained section of tissue in the implantation site at 16 weeks at (j) 1.25×, (k) 10× and (l) 20× magnification.

It was much more difficult to locate the implants in 16 weeks compared to 2 and 8 weeks as the implant protrusions observed during the excisions were minimised. As per 2 and 8 weeks no macroscopic evidence of adverse effects was present in the surrounding tissue. A small amount of solid tissue was present and attached to the suture. Tissue attached and surrounding the suture was dissected and processed for histology. Bisection of the harvested tissue revealed that the implants were much smaller in size and a very small amount of porous PEG sponges were remaining (FIG. 18a).

H&E staining was carried out to discern the tissue morphology and observe the presence of porous PEG sponges. Analysis of the H&E stained sections revealed that by 16 weeks, there was a minimal amount of porous PEG sponges remaining (FIG. 18b, c). Where there were remnants of porous PEG sponges, surrounding tissue was unremarkable dense cellular and vascular tissue. This indicates that in 16 weeks the polymer sponges undergo major degradation demonstrating their in vivo biodegradability.

Presence of macrophages and foreign body giant cells (FBGC) are an indication of innate immune responses towards an implant. As a means of determining macrophage and FBGC responses ED1 immunostaining was carried out on all the sections (FIG. 18d-l). ED1 staining of 2 week samples revealed the macrophage presence as predicted. Macrophages observed by the ED1 staining at 2 weeks were mainly present at the centre of the penetrated tissue with some located in the tissue/polymer interface (FIG. 18d-f). Analysis of the 8 weeks sections showed that the macrophage response had reduced significantly and the macrophages were much smaller in size (FIG. 18g-i). The tissue stained was dominated by non-inflammatory cells and were present in minimal numbers at scaffold/tissue interface, demonstrating the minimal response towards the hydrogel material. By 16 weeks the polymer sponges had undergone major degradation as evidenced by the very small amount of scaffold remaining. ED1 stained 16 weeks sections showed minimal number of macrophages (FIG. 20j-l). Analysis of the sections via ED1 staining that the porous PEG sponges and their degradation products initially result in a minor inflammatory response and this response is significantly reduced over 16 weeks.

The in vivo study revealed no adverse effects were observed in regards to the porous PEG sponges and their degradation products after 16 weeks of implantation. The porous PEG sponges demonstrate desirable properties as scaffolds by allowing vascular tissue penetration with minimal immunogenicity, and major degradation by 16 weeks.

It is to be understood that various other modifications and/or alterations may be made without departing from the spirit of the present invention as outlined herein.

Throughout this specification and the claims which follow, unless the context requires otherwise, the word "comprise", and variations such as "comprises" and "comprising", will be understood to imply the inclusion of a stated integer or step or group of integers or steps but not the exclusion of any other integer or step or group of integers or steps.

The reference in this specification to any prior publication (or information derived from it), or to any matter which is known, is not, and should not be taken as an acknowledgment or admission or any form of suggestion that that prior publication (or information derived from it) or known matter forms part of the common general knowledge in the field of endeavour to which this specification relates.

The invention claimed is:

1. A biodegradable polyether network polymer crosslinked via ester linkages which is prepared by polymerizing monomers consisting essentially of:
    (a) a multifunctional polyether monomer selected from the group consisting of glycerol ethoxylate and pentaerythritol ethoxylate,
    (b) a multifunctional crosslinking monomer selected from the group consisting of succinyl chloride, adipoyl chloride, sebacoyl chloride, glutaroyl chloride, pimeloyl chloride, suberoyl chloride and trimesoyl chloride, and
    (c) a mechanical property modifier which is dihydroxy poly(caprolactone), wherein the polyether monomer comprises a hydroxy functional group and the crosslinking monomer comprises a complementary functional group capable of reacting with the hydroxy functional group to form an ester linkage, and wherein the polyether monomer is branched.

2. A biodegradable polyether network polymer according to claim 1, wherein the crosslinking monomer is selected from the group consisting of succinyl chloride and sebacoyl chloride.

3. A biodegradable polyether network polymer according to claim 1, wherein the molar ratio of polyether monomer to crosslinking monomer in the polymerization reaction is in the range of from about 5:1 to 1:5.

4. A biodegradable polyether network polymer according to claim 1, wherein the monomers in the polymerization reaction comprise up to 20% (w/w) of the mechanical property modifier.

5. A process for preparing the biodegradable polyether network polymer crosslinked via ester linkages according to claim 1, the process comprising the step of polymerizing monomers consisting essentially of:

(a) a multifunctional polyether monomer selected from the group consisting of glycerol ethoxylate and pentaerythritol ethoxylate,
(b) a multifunctional crosslinking monomer selected from the group consisting of succinyl chloride, adipoyl chloride, sebacoyl chloride, glutaroyl chloride, pimeloyl chloride, suberoyl chloride and trimesoyl chloride, and
(c) a mechanical property modifier which is dihydroxy poly(caprolactone), wherein the monomers are polymerized under conditions allowing formation of ester linkages between the polyether monomer and the crosslinking monomer, wherein the polyether monomer comprises a hydroxy functional group and the crosslinking monomer comprises a complementary functional group capable of reacting with the hydroxy functional group to form an ester linkage, and wherein the polyether monomer is branched.

6. The process according to claim 5, wherein the molar ratio of polyether monomer to crosslinking monomer in the polymerization reaction is in the range of from about 5:1 to 1:5.

7. The process according to claim 5, wherein the monomers in the polymerization reaction comprise up to 20% (w/w) of the mechanical property modifier.

8. An ocular implant comprising a substrate comprising a biodegradable polyether network polymer according to claim 1 and cells selected from the group consisting of corneal epithelial cells and corneal endothelial cells seeded on the substrate.

9. A method of treating corneal endothelial dysfunction comprising the step of implanting an ocular implant in an eye of a subject, wherein the ocular implant comprises a substrate comprising a biodegradable polyether network polymer according to claim 1 and corneal endothelial cells seeded on the substrate.

10. A biodegradable polyether network polymer according to claim 1, wherein the polyether monomer is glycerol ethoxylate.

11. A biodegradable polyether network polymer according to claim 1, wherein the monomers in the polymerization reaction comprise the mechanical property modifier in an amount of from 0.1% to 15% (w/w).

12. A biodegradable polyether network polymer according to claim 1, wherein the monomers in the polymerization reaction comprise the mechanical property modifier in an amount of from 0.5% to 10% (w/w).

13. A biodegradable polyether network polymer according to claim 1, wherein the molar ratio of polyether monomer to crosslinking monomer in the polymerization reaction is in the range of from about 3:1 to 1:3.

14. A biodegradable polyether network polymer according to claim 1, wherein the molar ratio of polyether monomer to crosslinking monomer in the polymerization reaction is 1:2.

* * * * *

UNITED STATES PATENT AND TRADEMARK OFFICE
CERTIFICATE OF CORRECTION

PATENT NO. : 10,179,834 B2
APPLICATION NO. : 14/783838
DATED : January 15, 2019
INVENTOR(S) : Anton Blencowe et al.

Page 1 of 1

It is certified that error appears in the above-identified patent and that said Letters Patent is hereby corrected as shown below:

In the Specification

In Column 12, Line 43, change "polyther" to --polyether--.
In Column 13, Line 21, change "solublise" to --solubilise--.
In Column 17, Line 34, change "innerconnected" to --interconnected--.
In Column 19, Line 24, change "(99.5" to --(≥99.5 %),--.
In Column 29, Line 16 (Approx.), change "moduli." to --moduli--.
In Column 31, Line 65, change "(FIG." to --(FIGS.--.
In Column 32, Line 22, change "(FIG." to --(FIGS.--.
In Column 32, Line 67, change "(FIG." to --(FIGS.--.
In Column 33, Line 4, change "(FIG." to --(FIGS.--.
In Column 33, Line 7, change "(FIG." to --(FIGS.--.
In Column 33, Line 15, change "(FIG." to --(FIGS.--.
In Column 38, Line 67, change "(FIG." to --(FIGS.--.
In Column 39, Line 4, change "(FIG." to --(FIGS.--.
In Column 39, Line 22, change "(FIG." to --(FIGS.--.
In Column 39, Line 48, change "(FIG." to --(FIGS.--.
In Column 39, Line 57, change "(FIG." to --(FIGS.--.
In Column 39, Line 61, change "(FIG." to --(FIGS.--.
In Column 39, Line 64, change "(FIG." to --(FIGS.--.
In Column 40, Line 4, change "(FIG." to --(FIGS.--.
In Column 40, Line 29, change "that that" to --that--.

In the Claims

In Column 42, Line 24 (Approx.), Claim 14, change "poly ether" to --polyether--.

Signed and Sealed this
Fourth Day of June, 2019

Andrei Iancu
*Director of the United States Patent and Trademark Office*